(12) United States Patent
Elenitoba-Johnson et al.

(10) Patent No.: US 9,657,350 B2
(45) Date of Patent: May 23, 2017

(54) RNA CHIMERAS IN HUMAN LEUKEMIA AND LYMPHOMA

(71) Applicant: THE REGENTS OF THE UNIVERSITY OF MICHIGAN, Ann Arbor, MI (US)

(72) Inventors: Kojo Elenitoba-Johnson, Ann Arbor, MI (US); Thirunavukkarasu Velusamy, Ann Arbor, MI (US); Nallasivam Palanisamy, Ann Arbor, MI (US); Anagh Sahasrabuddhe, Ann Arbor, MI (US); Megan Lim, Ann Arbor, MI (US); Arul Chinnaiyan, Plymouth, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 70 days.

(21) Appl. No.: 14/271,175

(22) Filed: May 6, 2014

(65) Prior Publication Data
US 2014/0364481 A1 Dec. 11, 2014

Related U.S. Application Data

(60) Provisional application No. 61/831,385, filed on Jun. 5, 2013.

(51) Int. Cl.
*C12Q 1/68* (2006.01)
*G01N 33/574* (2006.01)

(52) U.S. Cl.
CPC ..... *C12Q 1/6886* (2013.01); *G01N 33/57426* (2013.01); *C12Q 2600/156* (2013.01)

(58) Field of Classification Search
None
See application file for complete search history.

(56) References Cited

PUBLICATIONS

Cain et al. (SciBX, 2013, p. 1-3; published Mar. 21, 2013).*
Velusamy et al. (PNAS, 2013, 110(8):3035-3040).*
Calin et al. "MiR-15a and miR-16-1 cluster functions in human leukemia." Proc Natl Acad Sci U S A. Apr. 1, 2008; 105(13):5166-71.
Castle et al., "Expression of 24,426 human alternative splicing events and predicted cis regulation in 48 tissues and cell lines." Nat Genet. Dec. 2008; 40(12):1416-25.
Christofk et al., "The M2 splice isoform of pyruvate kinase is important for cancer metabolism and tumour growth." Nature. Mar. 13, 2008;452(7184):230-3.
Cooper et al., "To metastasize or not? Selection of CD44 splice sites." Nat Med. Jul. 1995; 1(7):635-7.
de Klein, "A cellular oncogene is translocated to the Philadelphia chromosome in chronic myelocytic leukaemia." Nature. Dec. 23, 1982;300(5894):765-7.
Deininger et al., "The development of imatinib as a therapeutic agent for chronic myeloid leukemia." Blood. Apr. 1, 2005; 105(7):2640-53.
Dohner et al., "11q deletions identify a new subset of B-cell chronic lymphocytic leukemia characterized by extensive nodal involvement and inferior prognosis." Blood. Apr. 1, 1997; 89(7):2516-22.
Dohner et al., "Genomic aberrations and survival in chronic lymphocytic leukemia." N Engl J Med. Dec. 28, 2000; 343(26):1910-6.
Fabbri et al., "Analysis of the chronic lymphocytic leukemia coding genome: role of NOTCH1 mutational activation." J Exp Med. Jul. 4, 2011;208(7):1389-401.
Guerra et al., "A bicistronic CYCLIN D1-TROP2 mRNA chimera demonstrates a novel oncogenic mechanism in human cancer." Cancer Res. Oct. 1, 2008; 68(19):8113-21.
Hamblin et al., "Unmutated Ig V(H) genes are associated with a more aggressive form of chronic lymphocytic leukemia." Blood. Sep. 15, 1999; 94(6):1848-54.
Juliusson et al., "Prognostic subgroups in B-cell chronic lymphocytic leukemia defined by specific chromosomal abnormalities." N Engl J Med. Sep. 13, 1990; 323(11):720-4.
Klein, "The DLEU2/miR-15a/16-1 cluster controls B cell proliferation and its deletion leads to chronic lymphocytic leukemia." Cancer Cell. Jan. 19, 2010; 17(1):28-40.
Liu et al., "Cloning of two candidate tumor suppressor genes within a 10 kb region on chromosome 13q14, frequently deleted in chronic lymphocytic leukemia." Oncogene. Nov. 13, 1997;15(20):2463-73.
Maher et al., "Transcriptome sequencing to detect gene fusions in cancer." Nature. Mar. 5, 2009; 458(7234):97-101.
Matlin et al., "Understanding alternative splicing: towards a cellular code." Nat Rev Mol Cell Biol. May 2005; 6(5):386-98.
Mitelman, "Recurrent chromosome aberrations in cancer." Mutat Res. Apr. 2000; 462(2-3):247-53.
Orchard et al., "ZAP-70 expression and prognosis in chronic lymphocytic leukaemia." Lancet. Jan. 10, 2004; 363(9403):105-11.
Pajares et al., "Alternative splicing: an emerging topic in molecular and clinical oncology." Lancet Oncol. Apr. 2007; 8(4):349-57.
Prinos et al., "Alternative splicing of SYK regulates mitosis and cell survival." Nat Struct Mol Biol. Jun. 2011;18(6):673-9.
Puente et al., "Whole-genome sequencing identifies recurrent mutations in chronic lymphocytic leukaemia." Nature. Jun. 5, 2011; 475(7354):101-5.
Rabbitts, "Chromosomal translocations in human cancer." Nature. Nov. 10, 1994; 372(6502):143-9.
Rassenti et al., "ZAP-70 compared with immunoglobulin heavy-chain gene mutation status as a predictor of disease progression in chronic lymphocytic leukemia." N Engl J Med. Aug. 26, 2004; 351(9):893-901.
Rickman et al., "SLC45A3-ELK4 is a novel and frequent erythroblast transformation-specific fusion transcript in prostate cancer." Cancer Res. Apr. 1, 2009; 69(7):2734-8.

(Continued)

*Primary Examiner* — Stephanie K Mummert
(74) *Attorney, Agent, or Firm* — Casimir Jones, S.C.

(57) ABSTRACT

Provided herein are kits, compositions and methods for cancer diagnosis, research and therapy, including but not limited to, cancer markers. In particular, the present invention relates to recurrent RNA fusions as diagnostic markers and clinical targets for leukemia.

11 Claims, 23 Drawing Sheets

(56) References Cited

PUBLICATIONS

Rowley, "Chromosome translocations: dangerous liaisons revisited." Nat Rev Cancer. Dec. 2001; 1(3):245-50.
Rowley, "Letter: A new consistent chromosomal abnormality in chronic myelogenous leukaemia identified by quinacrine fluorescence and Giemsa staining." Nature. Jun. 1, 1973; 243(5405):290-3.
Rozman & Montserrat, "Chronic lymphocytic leukemia." N Engl J Med. Oct. 19, 1995; 333(16):1052-7.
Zhang et al., "Chimeric transcript generated by cis-splicing of adjacent genes regulates prostate cancer cell proliferation." Cancer Discov. Jul. 2012; 2(7):598-607.

* cited by examiner

```
                         SEQUENCE LISTING

<160> NUMBER OF SEQ ID NOS: 37

<210> SEQ ID NO 1
<211> LENGTH: 38
<212> TYPE: DNA
<213> ORGANISM: artificial sequence
<220> FEATURE:
<223> OTHER INFORMATION: Synthetic

<400> SEQUENCE: 1
agccggggtc gaaacgccgc gtgacttgta ggtgagag                             38

<210> SEQ ID NO 2
<211> LENGTH: 38
<212> TYPE: DNA
<213> ORGANISM: artificial sequence
<220> FEATURE:
<223> OTHER INFORMATION: Synthetic

<400> SEQUENCE: 2
tcctacactg cctccaagat ggtccaggct ggcataag                             38

<210> SEQ ID NO 3
<211> LENGTH: 38
<212> TYPE: DNA
<213> ORGANISM: artificial sequence
<220> FEATURE:
<223> OTHER INFORMATION: Synthetic

<400> SEQUENCE: 3
gacaagccgc tggcagccgc ggatctcacc gccgctca                             38

<210> SEQ ID NO 4
<211> LENGTH: 38
<212> TYPE: DNA
<213> ORGANISM: artificial sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: n is a, c, g, or t

<400> SEQUENCE: 4
ggaaacctcc atattcaaan aatctcagta aatctgta                             38

<210> SEQ ID NO 5
<211> LENGTH: 38
<212> TYPE: DNA
<213> ORGANISM: artificial sequence
<220> FEATURE:
<223> OTHER INFORMATION: Synthetic

<400> SEQUENCE: 5
ggcgcctgtg aaacgagtgg agatgagttc tgagcggt                             38

<210> SEQ ID NO 6
<211> LENGTH: 38
<212> TYPE: DNA
<213> ORGANISM: artificial sequence
<220> FEATURE:
```

```
<223> OTHER INFORMATION: Synthetic

<400> SEQUENCE: 6
ctgaacgtgg acagcctcat cacccggctg ctggaggg                              38

<210> SEQ ID NO 7
<211> LENGTH: 21
<212> TYPE: DNA
<213> ORGANISM: artificial sequence
<220> FEATURE:
<223> OTHER INFORMATION: Synthetic

<400> SEQUENCE: 7
ataccagctg aagagcgaca a                                                21

<210> SEQ ID NO 8
<211> LENGTH: 20
<212> TYPE: DNA
<213> ORGANISM: artificial sequence
<220> FEATURE:
<223> OTHER INFORMATION: Synthetic

<400> SEQUENCE: 8
agcctcgaac ttctgcttca                                                  20

<210> SEQ ID NO 9
<211> LENGTH: 20
<212> TYPE: DNA
<213> ORGANISM: artificial sequence
<220> FEATURE:
<223> OTHER INFORMATION: Synthetic

<400> SEQUENCE: 9
ctgaacgtgg acagcctcat                                                  20

<210> SEQ ID NO 10
<211> LENGTH: 21
<212> TYPE: DNA
<213> ORGANISM: artificial sequence
<220> FEATURE:
<223> OTHER INFORMATION: Synthetic

<400> SEQUENCE: 10
gagatgagtt ctgagcggtt g                                                21

<210> SEQ ID NO 11
<211> LENGTH: 20
<212> TYPE: DNA
<213> ORGANISM: artificial sequence
<220> FEATURE:
<223> OTHER INFORMATION: Synthetic

<400> SEQUENCE: 11
tgcaccacca actgcttagc                                                  20

<210> SEQ ID NO 12
<211> LENGTH: 21
<212> TYPE: DNA
<213> ORGANISM: artificial sequence
<220> FEATURE:
<223> OTHER INFORMATION: Synthetic

<400> SEQUENCE: 12
ggcatggact gtggtcatga g                                                21
```

```
<210> SEQ ID NO 13
<211> LENGTH: 20
<212> TYPE: DNA
<213> ORGANISM: artificial sequence
<220> FEATURE:
<223> OTHER INFORMATION: Synthetic

<400> SEQUENCE: 13
accagctgaa gagcgacaag                                              20

<210> SEQ ID NO 14
<211> LENGTH: 23
<212> TYPE: DNA
<213> ORGANISM: artificial sequence
<220> FEATURE:
<223> OTHER INFORMATION: Synthetic

<400> SEQUENCE: 14
cacaatcttt cctggacgac atc                                          23

<210> SEQ ID NO 15
<211> LENGTH: 17
<212> TYPE: DNA
<213> ORGANISM: artificial sequence
<220> FEATURE:
<223> OTHER INFORMATION: Synthetic

<400> SEQUENCE: 15
ccgccgctca ggtacga                                                 17

<210> SEQ ID NO 16
<211> LENGTH: 19
<212> TYPE: DNA
<213> ORGANISM: artificial sequence
<220> FEATURE:
<223> OTHER INFORMATION: Synthetic

<400> SEQUENCE: 16
acgtggacag cctcatcac                                               19

<210> SEQ ID NO 17
<211> LENGTH: 28
<212> TYPE: DNA
<213> ORGANISM: artificial sequence
<220> FEATURE:
<223> OTHER INFORMATION: Synthetic

<400> SEQUENCE: 17
gatatgatca aggaaaattc tgcccatt                                     28

<210> SEQ ID NO 18
<211> LENGTH: 16
<212> TYPE: DNA
<213> ORGANISM: artificial sequence
<220> FEATURE:
<223> OTHER INFORMATION: Synthetic

<400> SEQUENCE: 18
ctgctggagg gttttt                                                  16

<210> SEQ ID NO 19
<211> LENGTH: 500
<212> TYPE: DNA
<213> ORGANISM: artificial sequence
<220> FEATURE:
<223> OTHER INFORMATION: Synthetic
```

-continued

```
<400> SEQUENCE: 19
gctccgccag cttcgggctg cggccttccc tccgcttgca gtcgggaggg tgggcgtgcc      60
cttgcaaccc cttcctgta ccttctctgc aggtagatgg gacaaatgag tgtccggatc     120
agcgggagtg ggaaattgaa atactacaaa gatctgttta atcctgatac caactaatct    180 cccttcaag ggagagtctg ggaagctgta cagctcattt attttaaac ttttctgtt       240 tacagagatc tgttggtaat ctgaggattt ttattctacg tcgtcttgac agatggaaaa    300
cctgaagtaa cttcgggcta accttgtgtt tttggaaaat tagtagactt ggtggtgaag    360
aaactgggag gagtaggata ttagctaact ttgcatagcc acatatagag cgtcgcagct    420
gcattccacc aaagaggaac caaaaggcct gtggtgttcc cagggtacat attcatgcca    480
gaagtgaagt gctttggtga                                                500

<210> SEQ ID NO 20
<211> LENGTH: 500
<212> TYPE: DNA
<213> ORGANISM: artificial sequence
<220> FEATURE:
<223> OTHER INFORMATION: Synthetic

<400> SEQUENCE: 20
gtaagaagta aagtacaaag aatttagaat agtttctcta gaagcttata acttaatcaa     60
aagtcgtgga caaagtcgag caataatttt agcaagttat gagacgttag taaaatatat   120
gtagcttgga aaataatgtt acctggttgg atcattgcga actttctct agactaattt    180 cccttttctg ttttctattt aagtaatgag aaaataaac aggtttagaa aaagtgaaa      240 ggaaataagg ccaaaaatta tgaaagaag taattaaagc agctactacc ctctgaaaaa    300
cagtccacga gacatgaagg tagtcctagg tatatgtgtg cctaaaatat cattctaggt   360
ttaatggtga ataactatag agatcagtgt cagttttaag ataatcctgt gtagtaatgt   420
cagtgtaatg caggaactga accttagcta gacctgaagt tgctacttga cacttgagtc   480
gggaagccag acaggtaaat                                               500

<210> SEQ ID NO 21
<211> LENGTH: 23
<212> TYPE: DNA
<213> ORGANISM: artificial sequence
<220> FEATURE:
<223> OTHER INFORMATION: Synthetic

<400> SEQUENCE: 21 accccgggt gggctcaccc ggc                                              23

<210> SEQ ID NO 22
<211> LENGTH: 23
<212> TYPE: DNA
<213> ORGANISM: artificial sequence
<220> FEATURE:
<223> OTHER INFORMATION: Synthetic

<400> SEQUENCE: 22
gactcgggtg gccgaggggc ttc                                             23

<210> SEQ ID NO 23
<211> LENGTH: 526
<212> TYPE: DNA
<213> ORGANISM: artificial sequence
<220> FEATURE:
<223> OTHER INFORMATION: Synthetic
```

<400> SEQUENCE: 23

```
cgcaccgcgc gcctgcgcgg agagctgcgt gacgcggcgg cgcgcaaggg acgtgcggag      60
tgagtggcgc tgcgggtggg gccgtcggcg gcgctggtga gctttgcgga gctgggcggt     120
gccgaggagg aggaggtggc ggcctgggtc tgacgcggcc ctgttcgagg gggcctctct     180
tgtttattta tttattttcc gtgggtgcct ccgagtgtgc gcgcgctctc gctacccggc     240
ggggagggg tggggggagg gcccgggaaa aggggagtt ggagccgggg tcgaaacgcc      300
gcgtgacttg taggtgagag aacgccgagc cgtcgccgca gcctccgccg ccgagaagcc    360
cttgttcccg ctgctgggaa ggagagtctg tgccgacaag atggcggacg gggagctgaa    420
cgtggacagc ctcatcaccc ggctgctgga gggtgagtgc gcgcctggcc gcgggacaga   480
gggaggtcgg gcaccgccgc cgacccctgc gtcccgtct gccgcc                    526
```

<210> SEQ ID NO 24
<211> LENGTH: 27
<212> TYPE: DNA
<213> ORGANISM: artificial sequence
<220> FEATURE:
<223> OTHER INFORMATION: Synthetic

<400> SEQUENCE: 24

```
attgcccttg gctgcctccg attgtcg                                          27
```

<210> SEQ ID NO 25
<211> LENGTH: 29
<212> TYPE: DNA
<213> ORGANISM: artificial sequence
<220> FEATURE:
<223> OTHER INFORMATION: Synthetic

<400> SEQUENCE: 25

```
acagtacata tgcaatcgct ggacggcgg                                        29
```

<210> SEQ ID NO 26
<211> LENGTH: 693
<212> TYPE: DNA
<213> ORGANISM: artificial sequence
<220> FEATURE:
<223> OTHER INFORMATION: Synthetic

<400> SEQUENCE: 26

```
aaggaatagc ttttgtgaat ttcggactcc caactactag aattatgtga atcctgaatg     60
ataatcagat gtttactcag ttaagtgttt actcaaatat taataagtat tgatacattg    120
ggatgccatc ttatataatg attaacgaca cagattctgg gtgtatttca gccccagttt    180
cttctgcata tatgatagta agtgccttca aacaattctt gacacattaa aggtcagaaa    240
atgttagccg tcattattgc ttagtacaaa cctgagctag gaaatactaa cagagagctc    300
tttgtgccac tgagtcctgg aacttcccca tactaatttt gagaaggctt tcttgtaagt    360
atgtgacaga tactgtttcc tccacttct gtttattgca tataaccact attcttgtat    420
gtaagtacgt ataacagttt ctttactatt cccattattc agcgtttata atctggtttg    480
acatatcagt gttggtgctg agagggaaag gtatttctag gtaggataaa atggtgaaaa    540
gtgatttaac actgttgtat gcttgctttt ggccaggaac tatagggcag tgtatcttaa    600
actttgagtc ttgagaccct cttacactca aattctccat atatgtaaag aattgaaaac    660
gagcttttat ttatgtgagg tatttaacaa tat                                  693
```

<210> SEQ ID NO 27
<211> LENGTH: 33
<212> TYPE: DNA
<213> ORGANISM: artificial sequence
<220> FEATURE:
<223> OTHER INFORMATION: Synthetic

<400> SEQUENCE: 27
tgcaaacctg tcagtgagaa agagtgaggt ctg                          33

<210> SEQ ID NO 28
<211> LENGTH: 30
<212> TYPE: DNA
<213> ORGANISM: artificial sequence
<220> FEATURE:
<223> OTHER INFORMATION: Synthetic

<400> SEQUENCE: 28
ctcagcacca acactgatat gtcaaaccag                              30

<210> SEQ ID NO 29
<211> LENGTH: 489
<212> TYPE: DNA
<213> ORGANISM: artificial sequence
<220> FEATURE:
<223> OTHER INFORMATION: Synthetic

<400> SEQUENCE: 29
tcaggtgatc cacccacctc aacctcccaa ggtgctggga ttacaggcat gagccaccgt    60
gcccggccct gaaatctttt aagtctcttt ggctactagg ccccaggttg gtcacaggac   120
agcaaaaaac aggactgcat ttcatcaaca gcagacttga ggagcatcat caggaaccag   180
taacaatgaa aatagaagtc agagatcata gaataacatt attttaaacc atggaccaa    240 atagggtaat ttgctgcctg tgtgactttt ctgattttta agtatgggc atgactcttt    300 ttgaaagatt attatgagta aattttagaa aactgactgt tttatttatc gtttgtcagt    360
acgaggatgt cgtccaggaa agattgtgca gatgactgaa gcagaagttc gaggcttatg    420
tatcaagtct cgggagatct ttctcagcca gcctattctt ttggaattgg aagcaccgct    480
gaaaatttg                                                     489

<210> SEQ ID NO 30
<211> LENGTH: 26
<212> TYPE: DNA
<213> ORGANISM: artificial sequence
<220> FEATURE:
<223> OTHER INFORMATION: Synthetic

<400> SEQUENCE: 30
agtctctttg gctactaggc cccagg                                  26

<210> SEQ ID NO 31
<211> LENGTH: 30
<212> TYPE: DNA
<213> ORGANISM: artificial sequence
<220> FEATURE:
<223> OTHER INFORMATION: Synthetic

<400> SEQUENCE: 31
tacataccac aaattttcag cggtgcttcc                              30

<210> SEQ ID NO 32
<211> LENGTH: 20

```
<212> TYPE: DNA
<213> ORGANISM: Homo sapiens

<400> SEQUENCE: 32
gccgctcagg tacgaggatg                                          20

<210> SEQ ID NO 33
<211> LENGTH: 20
<212> TYPE: DNA
<213> ORGANISM: Homo sapiens

<400> SEQUENCE: 33
ctgctggagg agatctgttg                                          20

<210> SEQ ID NO 34
<211> LENGTH: 20
<212> TYPE: DNA
<213> ORGANISM: Homo sapiens

<400> SEQUENCE: 34
gccgctcagg tacgaggatg                                          20

<210> SEQ ID NO 35
<211> LENGTH: 21
<212> TYPE: DNA
<213> ORGANISM: Homo sapiens

<400> SEQUENCE: 35
ctgctggagg gtttttagaa c                                        21

<210> SEQ ID NO 36
<211> LENGTH: 49
<212> TYPE: DNA
<213> ORGANISM: Homo sapiens

<400> SEQUENCE: 36
ccgcggatct caccgccgct caggtacgag gatgtcgtcc aggaaagat           49

<210> SEQ ID NO 37
<211> LENGTH: 66
<212> TYPE: DNA
<213> ORGANISM: Homo sapiens

<400> SEQUENCE: 37
gtggacagcc tcatcacccg gctgctggag ggtttttaga acttcagcca taaaaatggg    60
cagaat                                                         66
```

RNA CHIMERAS IN HUMAN LEUKEMIA AND LYMPHOMA

This application claims priority to U.S. Pat. Appl. Ser. No. 61/831,385, filed Jun. 5, 2013, which is incorporated herein by reference in its entirety.

STATEMENT REGARDING FEDERALLY SPONSORED RESEARCH OR DEVELOPMENT

This invention was made with government support under CA136905, DE019249 and CA140806 awarded by the National Institutes of Health. The government has certain rights in the invention.

FIELD OF THE INVENTION

Provided herein are kits, compositions and methods for cancer diagnosis, research and therapy, including but not limited to, cancer markers. In particular, the present invention relates to recurrent RNA fusions as diagnostic markers and clinical targets for leukemia.

BACKGROUND OF THE INVENTION

A central aim in cancer research is to identify altered genes that are causally implicated in oncogenesis. Several types of somatic mutations have been identified, including base substitutions, insertions, deletions, translocations, and chromosomal gains and losses, all of which result in altered activity of an oncogene or tumor suppressor gene. First hypothesized in the early 1900's, there is now compelling evidence for a causal role for chromosomal rearrangements in cancer (Rowley, *Nat Rev Cancer* 1: 245 (2001)). Recurent chromosomal aberrations were thought to be primarily characteristic of leukemias, lymphomas, and sarcomas. Epithelial tumors (carcinomas), which are much more common and contribute to a relatively large fraction of the morbidity and mortality associated with human cancer, comprise less than 1% of the known, disease-specific chromosomal rearrangements (Mitelman, *Mutat Res* 462: 247 (2000)). While hematological malignancies are often characterized by balanced, disease-specific chromosomal rearrangements, most solid tumors have a plethora of non-specific chromosomal aberrations. It is thought that the karyotypic complexity of solid tumors is due to secondary alterations acquired through cancer evolution or progression.

Two primary mechanisms of chromosomal rearrangments have been described. In one mechanism, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to MYC leading to activation of this oncogene in B- and T-cell malignancies, respectively (Rabbitts, *Nature* 372: 143 (1994)). In the second mechanism, rearrangement results in the fusion of two genes, which produces a fusion protein that may have a new function or altered activity. The prototypic example of this translocation is the BCR-ABL gene fusion in chronic myelogenous leukemia (CML) (Rowley, *Nature* 243: 290 (1973); de Klein et al., *Nature* 300: 765 (1982)). Importantly, this finding led to the rational development of imatinib mesylate (Gleevec), which successfully targets the BCR-ABL kinase (Deininger et al., *Blood* 105: 2640 (2005)). Thus, identifying recurrent rearrangements in common tumors may have profound implications for cancer diagnosis, drug discovery efforts, as well as patient treatment.

SUMMARY OF THE INVENTION

Provided herein are kits, compositions and methods for cancer diagnosis, research and therapy, including but not limited to, cancer markers. In particular, the present invention relates to recurrent RNA fusions as diagnostic markers and clinical targets for leukemia.

Embodiments of the present invention provide accurate and specific compositions and methods for diagnosing and treating B-cell chronic lymphocytic leukemia.

For example, in some embodiments, the present inventions provides a kit for detecting RNA fusions associated with B-cell chronic lymphocytic leukemia in a subject, comprising, consisting essentially of, or consisting of: at least a first RNA fusion informative reagent for identification of an yippee-like 5 (Genbank accession number NM_001127401)—protein phosphatase 1, catalytic subunit, beta isozyme (Genbank accession number NM_001244974) (YPEL5-PPP1CB) or PPP1CB-YPEL5 RNA fusion. The present invention is not limited to a specific RNA fusion informative reagent. Examples include, but are not limited to, a probe that specifically hybridizes to the fusion junction of an YPEL5-PPP1CB or PPP1CB-YPEL5 RNA fusion, a pair of primers that amplify a fusion junction of an YPEL5-PPP1CB or PPP1CB-YPEL5 RNA fusion (e.g., a first primer that hybridizes to a YPEL5 nucleic acid and second primer that hybridizes to a PPP1CB nucliec acid), an antibody that binds to a truncated PPP1CB polypeptide, a sequencing primer that binds to a YPEL5-PPP1CB or PPP1CB-YPEL5 RNA fusion and generates an extension product that spans the fusion junction of the YPEL5-PPP1CB or PPP1CB-YPEL5 RNA fusion, or probes wherein the first probe hybridizes to a YPEL5 nucleic acid and said second probe hybridizes to a PPP1CB nucleic acid. In some embodiments, the reagent is labeled. In some embodiments, the kit further comprises controls (e.g., RNA fusion controls or cDNA equivalents thereof).

In some embodiments, the present invention provides a reaction mixture comprising one or more RNA fusion informative reagents for identification of an yippee-like 5 (Genbank accession number NM_001127401)—protein phosphatase 1, catalytic subunit, beta isozyme (Genbank accession number NM_001244974) (YPEL5-PPP1CB) or PPP1CB-YPEL5 RNA fusion complexed to an RNA fusion.

Further embodiments of the present invention provide a method for diagnosing, monitoring, or identifying a risk of B-cell chronic lymphocytic leukemia in a subject, comprising: (a) contacting a biological sample from a subject with at least a first RNA fusion informative reagent for identification of an YPEL5-PPP1CB or PPP1CB-YPEL5 RNA fusion (e.g., those described herein); and (b) diagnosing, monitoring, or identifying a risk of B-cell chronic lymphocytic leukemia in the subject when the YPEL5-PPP1CB or PPP1CB-YPEL5 RNA fusion is present in the sample. In some embodiments, the YPEL5-PPP1CB RNA fusion comprises exon 1 of YPEL5 and exon 2 of PPP1CB. In some embodiments, the YPEL5-PPP1CB RNA fusion encodes a truncated PPP1CB polypeptide. In some embodiments, the truncated PPP1CB polpeptide consists of residue 29 to residue 327 of wild type PPP1CB. In some embodiments, the PPP1CB-YPEL5 RNA fusion comprises exon 1 of PPP1CB and exon 3 of YPEL5. In some embodiments, the PPP1CB-YPEL5 RNA fusion encodes full-length wild-type YPEL5 protein. In some embodiments, the reagent is mass spectrometry reagents for identifying a truncated PPP1CB polypepeptide or reagents for performing a PPP1CB activity assay. In some embodiments, the method further comprises the step of collecting the sample from the subject. In some embodiments, the sample is, for example, tissue, blood, plasma, serum, or cells. In some embodiments, diagnosing distinguishes B-cell chronic lymphocytic leukemia from other types of leukemia. In some embodiments, the method further comprises performing the method in combination with an additional leukemia detection assay (e.g., detecting a chromosomal duplication, detecting a chromosomal deletion, or detecting aberrant NOTCH family member activity). In some embodiments, the method further comprises the step of treating the subject for B-cell chronic lymphocytic leukemia. In some embodiments, the method is performed prior to or during treatment for B-cell chronic lymphocytic leukemia. In some embodiments, the method is used to determine (e.g., stop, start, or alter) a treatment course of action for B-cell chronic lymphocytic leukemia.

The present invention additionally provides the use of least a first RNA fusion informative reagent for identification of a YPEL5-PPP1CB or PPP1CB-YPEL5 RNA fusion in the diagnosis of B-cell chronic lymphocytic leukemia (e.g., the reagents described herein).

The present invention further provides a method of treating B-cell chronic lymphocytic leukemia, comprising: inhibiting the expression or activity of a YPEL5-PPP1CB RNA fusion or a truncated PPP1CB polypeptide expressed from the fusion in a B-cell chronic lymphocytic leukemia cell. In some embodiments, the inhibiting comprises one or more of contacting the cell with an siRNA or antisense nucleic acid that specifically binds to a YPEL5-PPP1CB RNA fusion, genetic therapy that increases expression of wild type PPP1CB, or reducing expression of truncated PPP1CB.

Additional embodiments of the present invention are provided in the description and examples below.

DEFINITIONS

Figure 1:
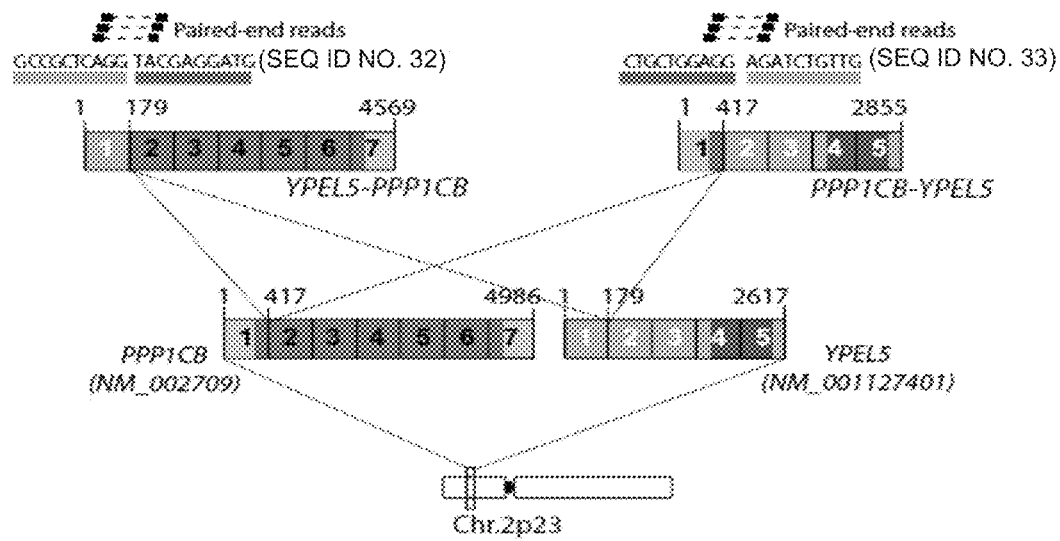
FIG. 1 shows YPEL5/PPP1CB and PPP1CB/B YPEL5 fusions in CLL. (A) Mate-pair read mapping depicts the occurrence of YPEL5/PPP1CB and PPP1CB/YPEL5 chimera in CLL index samples. (B) Q real-time PCR validation of fusion transcripts in index CLL samples. (C) Recurrent expression of YPEL5/PPP1CB and PPP1CB/YPEL5 in CLL. SYBR green-based q real-time PCR analysis was performed in seven independent CLL cases other than index samples for detection of YPEL5/PPP1CB and PPP1CB/YPEL5 and compared with different lymphoma-derived cell lines and solid tumors, such as prostate (Pros), gastric (Gas), and melanoma (Mel). (D) Sequence traces obtained by Sanger sequencing of the PCR amplicons obtained using YPEL5 and PPP1CB primers designed to amplify across the chimeric fusion transcripts.
Figure 1:
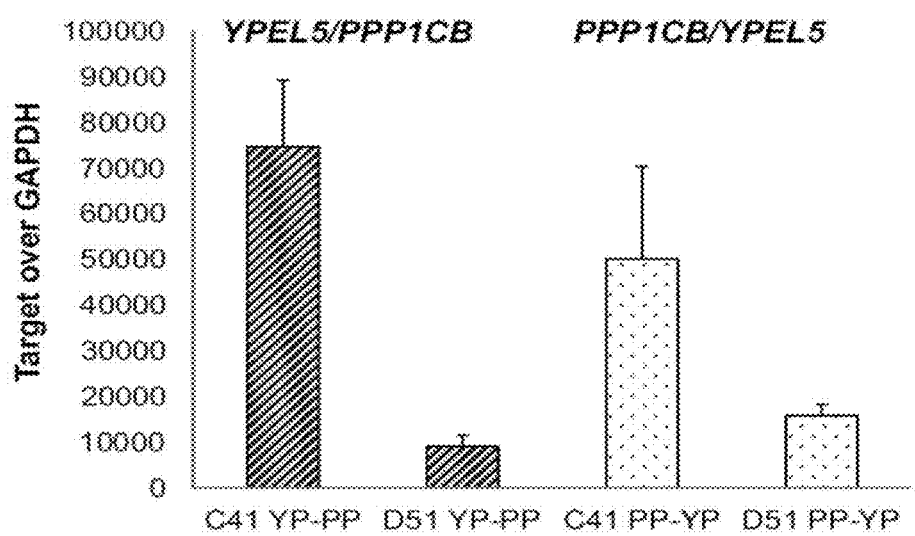
Figure 1:
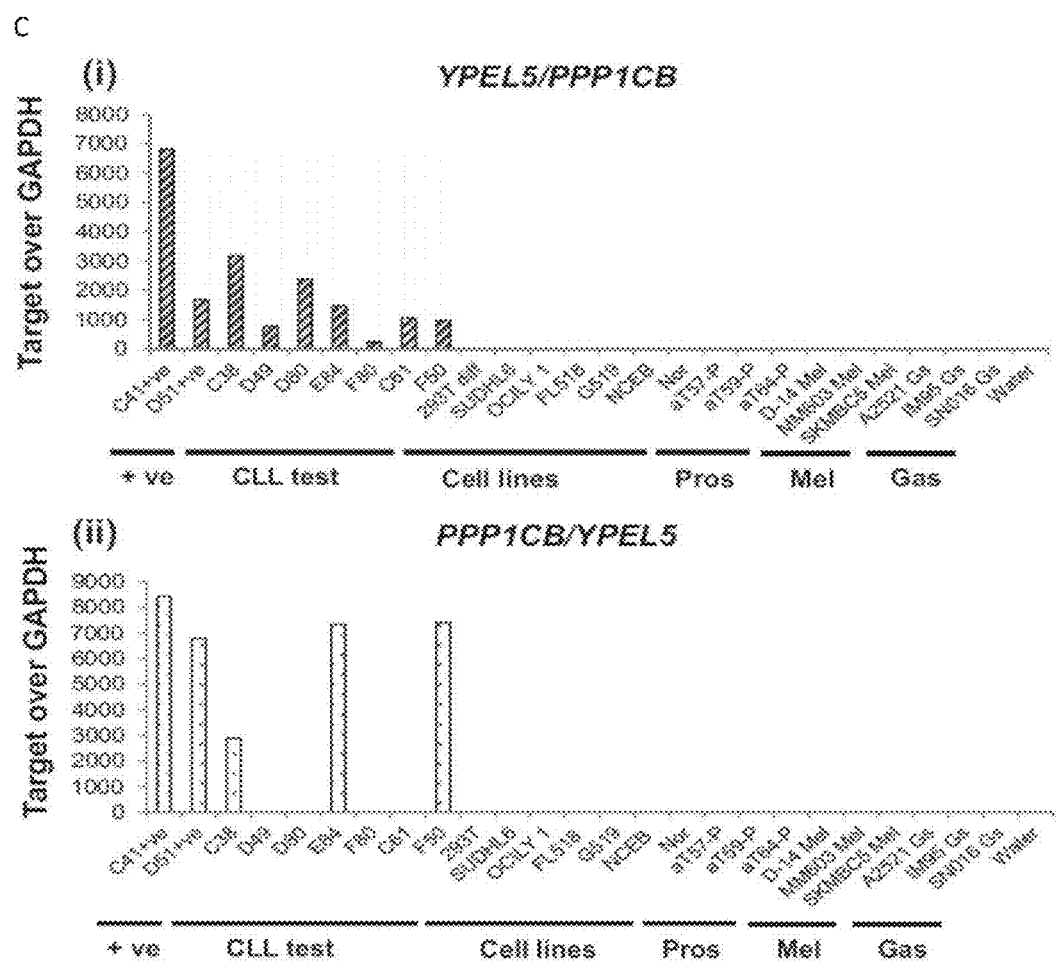

To facilitate an understanding of the present invention, a number of terms and phrases are defined below:

As used herein, the term "RNA fusion" refers to a chimeric messenger RNA (mRNA) resulting from the fusion of at least a portion of a first mRNA to at least a portion of a second mRNA. The fusion need not include entire transcripts of genes.

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the terms "CLL informative reagent" refers to a reagent or reagents that are informative for identification of mRNA fusions described herein (e.g., YPEL5-PPP1CB or PPP1CB-YPEL5 fusions). In some embodiments, reagents are primers, probes or antibodies for detection of mRNA fusions or proteins expressed from mRNA fusions described herein.

As used herein, the term "transcriptional regulatory region" refers to the non-coding upstream regulatory sequence of a gene, also called the 5' untranslated region (5' UTR).

As used herein, the terms "detect", "detecting", or "detection" may describe either the general act of discovering or discerning or the specific observation of a detectably labeled composition.

As used herein, the term "inhibits at least one biological activity of a RNA fusion" refers to any agent that decreases any activity of a RNA fusion of the present invention (e.g., including, but not limited to, the activities described herein) or a protein expressed from the RNA fusion, via directly contacting chimeric proteins, contacting mRNA fusions, causing conformational changes of fusion polypeptides, decreasing mRNA levels, or interfering with interactions with signaling partners, and affecting the expression of or activity of or funsion of proteins expressed from RNA fusions. Inhibitors also include molecules that indirectly regulate fusion biological activity by intercepting upstream signaling molecules.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "antisense compound" refers to an oligomeric compound that is at least partially complementary to a target nucleic acid molecule to which it hybridizes. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds.

As used herein, the term "antisense oligonucleotide" refers to an antisense compound that is an oligonucleotide.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous."

The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature)

sequences with single base mismatches. In other words, under conditions of high stringency the temperature can be raised so as to exclude hybridization to sequences with single base mismatches.

As used herein, the term "amplification oligonucleotide" refers to an oligonucleotide that hybridizes to a target nucleic acid, or its complement, and participates in a nucleic acid amplification reaction. An example of an amplification oligonucleotide is a "primer" that hybridizes to a template nucleic acid and contains a 3' OH end that is extended by a polymerase in an amplification process. Another example of an amplification oligonucleotide is an oligonucleotide that is not extended by a polymerase (e.g., because it has a 3' blocked end) but participates in or facilitates amplification. Amplification oligonucleotides may optionally include modified nucleotides or analogs, or additional nucleotides that participate in an amplification reaction but are not complementary to or contained in the target nucleic acid. Amplification oligonucleotides may contain a sequence that is not complementary to the target or template sequence. For example, the 5' region of a primer may include a promoter sequence that is non-complementary to the target nucleic acid (referred to as a "promoter-primer"). Those skilled in the art will understand that an amplification oligonucleotide that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligonucleotide may provide a promoter sequence and serve as a template for polymerization (referred to as a "promoter-provider").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular nucleic acid sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, including biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. These examples are not to be construed as limiting the sample types applicable to the present invention

DETAILED DESCRIPTION OF THE INVENTION

Provided herein are kits, compositions and methods for cancer diagnosis, research and therapy, including but not limited to, cancer markers. In particular, the present invention relates to recurrent RNA fusions as diagnostic markers and clinical targets for leukemia.

B-cell chronic lymphocytic leukemia (B-CLL) is the most common form of leukemia in adults in Western countries (Rozman, (1995) N Engl J Med 333(16): 1052-1057). The most common recurrent cytogenetic abnormality in CLL is a deletion involving the 13q14.3 locus, which occurs in 50% of cases and targets miR-16-1, miR-15a, and DLEU2 (Calin G A, et al. (2008) Proc Natl Acad Sci USA 105(13):5166-5171; Klein, et al. (2010) Cancer Cell 17(1):28-40; Liu, et al. (1997) Oncogene 15(20):2463-2473). Twenty percent of CLLs exhibit trisomy 12 (Juliusson G, et al. (1990) N Engl J Med 323(11):720-724). Other recurrent abnormalities in CLL include del 11q22-23 (ATM) and 17p13 (targeting p53) (Döhner H, et al. (2000) N Engl J Med 343(26):1910-1916; Döhner H, et al. (1997) Blood 89(7):2516-2522). Of clinical relevance, IgV mutational status and zeta-chain associated protein kinase-70 kD (ZAP-70) expression have been associated with distinct prognostic categories of B-CLL (Orchard J A, et al. (2004) Lancet 363(9403):105-111; Rassenti L Z, et al. (2004) N Engl J Med 351(9):893-901; Hamblin et al., (1999) Blood 94(6):1848-1854). Recently, mutations in NOTCH1 (12.2%), MYD88 (2.9%), and XPO1 (2.4%) have been identified using next-generation sequencing (Puente X S, et al. (2011) Nature 475(7354):101-105; Fabbri G, et al. (2011) J Exp Med 208(7):1389-1401). The NOTCH1 mutations occur more frequently in cases with unmutated variable regions of the Ig heavy chain genes, whereas the MYD88 mutations occur more frequently in mutated cases (Puente et al., supra).

Although the role of genomic events is well established in the pathogenesis of cancers, the contribution of posttranscriptional RNA processing, which plays a fundamental role in control of protein expression, is less well understood. Alternative splicing can affect the translation, localization, or degradation of mRNA (Matlin et al., (2005) Nat Rev Mol Cell Biol 6(5):386-398) and frequently results in the production of multiple and functionally distinct protein isoforms (Castle J C, et al. (2008) Nat Genet 40(12):1416-1425). Alternative splicing and expression of abnormal splicing chimeras may contribute to cancer pathogenesis and are associated with prognostic significance (Pajares M J, et al. (2007) Lancet Oncol 8(4):349-357; Guerra E, et al. (2008) Cancer Res 68(19):8113-8121). For example, alternative splicing of CD44 has been associated with enhancement of metastatic potential (Cooper D L, Dougherty G J (1995) Nat Med 1(7):635-637). Similarly, the glycolytic enzyme pyruvate kinase M is known to undergo alternative splicing to yield a protein product (PKM2) that regulates cancer metabolism (Christofk H R, et al. (2008) The M2 splice isoform of pyruvate kinase is important for cancer metabolism and tumour growth. Nature 452(7184):230-233). Alternative splicing of the tyrosine kinase SYK has been shown to promote oncogenesis in ovarian cancer cells (Prinos P, et al. (2011) Nat Struct Mol Biol 18(6):673-679). Chimeric transcripts that exert oncogenic effects have been described. Expression of an RNA chimera fusing CCND1 and TROP2 (TACSTD2) transcripts has been demonstrated to result in immortalization and transformation of human epithelial cells (Guerra et al., supra). Reciprocal RNA splicing chimeras that are recurrent in specific forms of cancer have not been described. However, recent studies using next-generation sequencing have identified a recurrent non-reciprocal chimera involving SLC45A3 and ELK4 in prostate cancer by a cis-splicing mechanism without DNA-level rearrangement (Zhang Y, et al. (2012) Cancer Discov 2(7): 598-607; Rickman D S, et al. (2009) Cancer Res 69(7): 2734-2738; Maher C A, et al. (2009) Nature 458(7234):97-101).

Experiments conducted during the course of development of embodiments of the present invention identified recurrent reciprocal chimeric transcripts between YPEL5 and PPP1CB genes in CLL using whole-transcriptome sequencing. Whole-genome sequencing and extensive Southern blotting analyses revealed the wild-type configuration at both YPEL5 and PPP1 CB gene loci, indicating that the chimeras resulted from RNA splicing events rather than a chromosomal rearrangement. Evaluation of the presence of the chimeric fusion by quantitative real-time PCR (q real-time PCR) in diverse hematopoietic neoplasia, normal B- and T-cell subsets, and nonlymphoid malignancies revealed selective expression of the chimeras in CLL. The RNA fusion chimera resulted in a truncated PPP1 CB protein product with reduced enzymatic activity. Reduced expression of PPP1CB protein further enhanced the oncogenic phenotype in MEC1 and JVM3 B-cell leukemia cells. These results describe a role for RNA splicing chimeras in the pathogenesis of CLL.

The compositions and method described herein meet an unmet need for diagnostic and therapeutic targets in CLL. The mRNA fusions described herein specifically identify greater than 90% of pateints with CLL veruses other leukemias. Thus, the compositions and methods described herein find use in differential diagnosis of CLL, which allows for the use of treatements specific for CLL. In addition, the overexpression of truncated PPP1CB has a causative effect in CLL, which provides a therapeutic target for treatment of CLL.

I. mRNA Fusions

Embodiments of the present invention provide diagnostic, screening, research, and therapeutic method of diagnosing and characterizing cancer (e.g., based on the presence of YPEL5-PPP1CB or PPP1CB-YPEL5 mRNA fusions or assoicationed protiens in a sample). In some embodiments, fusions are reciprocal YPEL5-PPP1CB or PPP1CB-YPEL5 fusions of the noncoding exon 1 of YPEL5 juxtaposed to exon 2 of PPP1CB or exon 1 of PPP1CB juxtaposed to exon 3 of YPEL5, although other regions are specifically encompassed by embodiments of the present invention. In some embodiments, the presence of YPEL5-PPP1CB or PPP1CB-YPEL5 is detected by detecting truncated PPP1 CB proteins in a sample Exemplary nucleic acid and protein detection methods are described below.

II. Antibodies

Proteins expressed from RNA fusions, including fragments, derivatives and analogs thereof, may be used as immunogens to produce antibodies having use in the diagnostic, research, and therapeutic methods described below. The antibodies may be polyclonal or monoclonal, chimeric, humanized, single chain or Fab fragments. Various procedures may be used for the production and labeling of such antibodies and fragments. See, e.g., Burns, ed., *Immunochemical Protocols*, 3$^{rd}$ ed., Humana Press (2005); Harlow and Lane, Antibodies: *A Laboratory Manual*, Cold Spring Harbor Laboratory (1988); Kozbor et al., *Immunology Today* 4: 72 (1983); Köhler and Milstein, *Nature* 256: 495 (1975).

III. Diagnostic and Screening Applications

Embodiments of the present invention provides RNA and protein based diagnostic methods that either directly or indirectly detect the RNA fusions. In some embodiments, the present invention also provides compositions and kits for diagnostic purposes.

The diagnostic methods of the present invention may be qualitative or quantitative. Quantitative diagnostic methods may be used, for example, to discriminate between indolent and aggressive cancers via a cutoff or threshold level. Where applicable, qualitative or quantitative diagnostic methods may also include amplification of target, signal or intermediary (e.g., a universal primer).

An initial assay may confirm the presence of a RNA fusion but not identify the specific fusion. A secondary assay is then performed to determine the identity of the particular fusion, if desired. The second assay may use a different detection technology than the initial assay.

The RNA fusions of embodiments of the present invention may be detected along with other markers for CCL in a multiplex or panel format. Markers are selected for their predictive value alone or in combination with the RNA fusions. Markers for other cancers, diseases, infections, and metabolic conditions are also contemplated for includsion in a multiplex of panel format.

In some embodiments, additional diagnostic assays useful in the diagnosis or characterization of CCL are performed in combination with assays for detection of RNA fusions associated with CCL. Examples include, but are not limited to, chromosomal deletions (e.g., deletions chromosomes 13, 11, or 17), chromosomal duplications (e.g., trisomy 12), chromosomal translocations (e.g., between chromosomes 11 and 14), and alterations in NOTCH family member signaling (e.g., due to mutations in NOTCH family member genes). In some embodiments, the loss of part of chromosome 13 is linked with a slower growing disease and a better outlook, while defects in chromosomes 11 or 17 often indicate a poorer outlook.

The diagnostic methods of embodiments of the present invention may also be modified with reference to data correlating particular RNA fusions with the stage, aggressiveness or progression of the disease or the presence or risk of metastasis. Ultimately, the information provided by the methods of the present invention will assist a physician in choosing the best course of treatment for a particular patient.

A. Sample

Any patient sample suspected of containing the RNA fusions may be tested according to the methods of the present invention. By way of non-limiting examples, the sample may be blood, or a fraction thereof (e.g., plasma, serum, or cells).

In some embodiments, the patient sample typically requires preliminary processing designed to isolate or enrich the sample for the RNA fusions or cells that contain the RNA fusions. A variety of techniques may be used for this purpose, including but not limited: centrifugation; immunocapture; cell lysis; and, nucleic acid target capture.

B. RNA Detection

In some embodiments, the RNA fusions of embodiments of the present invention are detected as mRNA using a variety of nucleic acid techniques, including but not limited to: nucleic acid sequencing; nucleic acid hybridization; and, nucleic acid amplification. In some embodiments, mRNA is converted to cDNA prior to detection (e.g., using reverse transcription techniques described herein).

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, fluorescent or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

Some embodiments of the present invention utilize next generation or high-throughput sequencing. A variety of nucleic acid sequencing methods are contemplated for use in the methods of the present disclosure including, for example, chain terminator (Sanger) sequencing, dye terminator sequencing, and high-throughput sequencing methods. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques can be used including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005

Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, capillary electrophoresis (CE) is utilized to analyze amplification fragments. During capillary electrophoresis, nucleic acids (e.g., the products of a PCR reaction) are injected electrokinetically into capillaries filled with polymer. High voltage is applied so that the fluorescent DNA fragments are separated by size and are detected by a laser/camera system. In some embodiments, CE systems from Life Technogies (Grand Island, N.Y.) are utilized for fragment sizing (See e.g., U.S. Pat. No. 6,706,162, U.S. Pat. No. 8,043,493, each of which is herein incorporated by reference in its entirety).

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary RNA strand as a probe to localize a specific RNA sequence in a portion or section of tissue (in situ), or, if the tissue is small enough, the entire tissue (whole mount ISH). RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

2.1 FISH

In some embodiments, fusion mRNA sequences are detected using fluorescence in situ hybridization (FISH). In some embodiments, FISH assays for the present invention utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor. In some embodiments, the detection assay is a FISH assay utilizing a probe for YPEL5-PPP1CB or PPP1CB-YPEL5 fusion mRNAs.

2.2 Microarrays

Different kinds of biological assays are called microarrays including, but not limited to: RNA microarrays (e.g., mRNA or cDNA microarrays and oligonucleotide microarrays); protein microarrays; tissue microarrays; transfection or cell microarrays; chemical compound microarrays; and, antibody microarrays. A RNA or DNA microarray, commonly known as gene chip, RNA or DNA chip, or biochip, is a collection of microscopic RNA or DNA spots attached to a solid surface (e.g., glass, plastic or silicon chip) forming an array for the purpose of expression profiling or monitoring expression levels for thousands of genes simultaneously. The affixed nucleic acid segments are known as probes, thousands of which can be used in a single microarray. Microarrays can be used to identify disease genes by identifying fusion sequences in disease cells. Microarrays can be fabricated using a variety of technologies, including but not limiting: printing with fine-pointed pins onto glass slides; photolithography using pre-made masks; photolithography using dynamic micromirror devices; ink jet printing; or, electrochemistry on microelectrode arrays.

Northern blotting is used to detect specific RNA sequences, respectively. RNA extracted from a sample is fragmented, electrophoretically separated on a matrix gel, and transferred to a membrane filter. The filter bound RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

In some embodiments, chimeric mRNA is amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and U.S. Pat. No. 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified RNA fusion nucleic acids or DNA reverse transcribed from such fusions can be detected by any means. For example, the RNA fusions can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification including methods disclosed in U.S. Pat. Nos. 6,303,305 and 6,541,205, each of which is herein incorporated by reference in its entirety can be used. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DAB-CYL and EDANS). Molecular beacons are disclosed in U.S. Pat. Nos. 5,925,517 and 6,150,097, herein incorporated by reference in its entirety.

Other self-hybridizing are, for example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

C. Protein Detection

In some embodiments, the RNA fusions of embodiments of the present invention are detected as truncated or chimeric proteins using a variety of protein techniques, including but not limited to: protein sequencing, mass spectrometyr, and immunoassays.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

2. Immunoassays

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

In some embodiments, immunoassays differentiate between truncated PPP1CB and wild type PPP1CB. For example, in some embodiments, two antibodies with different labels are used: one that binds only to the portion of PPP1CB that is truncated and one that binds to the retained portion of the protein. The relative amounts of the two antibodies are compared to detect the presence or absence of truncated PPP1CB. For example, if only the antibody that binds to the retained portion of PPP1CB is detected, and the antibody that binds to the truncatd portion is not detected, then truncated PPP1CB is present. If both antibodies are detected, then wild type PPP1CB is present. In some embodiments, a single antibody that binds only to truncatd PPP1CB is utilized.

D. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a serum, blood, or cell sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a cellular or other biological sample, the subject may visit a medical center to have the sample obtained and sent to the profiling center, or subjects may collect the sample themselves and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (e.g., presence or absence of an RNA fusion), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

E. In vivo Imaging

The RNA fusions of the present invention may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention. In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. Sumerdon et al., (Nucl. Med. Biol 17:247-254 [1990] have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having recurrent colorectal cancer. Agents with paramagnetic ions as labels for magnetic resonance imaging can be utilized (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

F. Compositions & Kits

Compositions for use in the diagnostic methods of the present invention include, but are not limited to, probes, sequencing primer(s), amplification oligonucleotides, and antibodies. Particularly preferred compositions detect a product only when a YPEL5-PPP1CB or PPP1CB-YPEL5 fusion is present in a sample. These compositions include: a single labeled probe comprising a sequence that hybridizes to the junction at which a 5' portion from a YPEL5 mRNA fuses to a 3' portion from a PPP1 CB mRNA or a 5' portion of a PP1CB mRNA fuses to a 3' portion from a YPEF5 mRNA (i.e., spans the fusion junction); a pair of amplification oligonucleotides wherein the first amplification oligonucleotide comprises a sequence that hybridizes to YPEF5 mRNA or cDNA synthesized from the mRNA and the second amplification oligonucleotide comprises a sequence that hybridizes to YPEF5 mRNA or cDNA synthesized from the mRNA; an antibody that specifically binds to a truncated PPP1CB protein.

Any of these compositions, alone or in combination with other compositions of the present invention, may be provided in the form of a kit. For example, the single labeled probe and pair of amplification oligonucleotides may be provided in a kit for the amplification and detection of RNA fusions of the present invention. Kits may further comprise appropriate controls and/or detection reagents.

The probe and antibody compositions of the present invention may also be provided in the form of an array.

IV. Drug Screening Applications

In some embodiments, the present invention provides drug screening assays (e.g., to screen for anticancer drugs). The screening methods of the present invention utilize cancer markers identified using the methods of the present invention (e.g., including but not limited to YPEL5-PPP1CB or PPP1CB-YPEL5 mRNA fusions). For example, in some embodiments, the present invention provides methods of screening for compounds that alter (e.g., decrease) the expression of proteins expressed from RNA fusions described herein. The compounds or agents may interfere with transcription, by interacting, for example, with the promoter region. The compounds or agents may interfere with mRNA produced from the fusion (e.g., by RNA interference, antisense technologies, etc.). The compounds or agents may interfere with pathways that are upstream or downstream of the biological activity of the fusion. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present invention and inhibit its biological function.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of polypeptide is assayed for by detecting the level of cancer marker mRNA expressed by the cell. mRNA expression can be detected by any suitable method. In other embodiments, the effect of candidate compounds on expression of RNA fusions is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., polypeptides expressed from RNA fusions) either directly or indirectly in a therapeutic protocol, to elaborate the biological function of the target gene product, or to identify compounds that disrupt normal target gene interactions. Compounds that inhibit the activity or expression of RNA fusions are useful in the treatment of proliferative disorders, e.g., cancer, particularly CCL.

In one embodiment, the invention provides assays for screening candidate or test compounds that are substrates of a cancer marker protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

VI. Therapeutic and Research Applications

In some embodiments, the present invention provides therapies and research reagents for treating, monitoring, and investigated cancer (e.g., CCL). In some embodiments, therapies directly or indirectly target cancer markers (e.g., including but not limited to, YPEL5-PPP1CB or PPP1CB-YPEL5 mRNA fusions).

A. RNA Interference and Antisense Therapies

In some embodiments, the present invention targets the expression of cancer markers. For example, in some embodiments, the present invention employs compositions comprising oligomeric antisense or RNAi compounds, particularly oligonucleotides (e.g., those identified in the drug screening methods described above), for use in modulating the function of nucleic acid molecules encoding cancer markers of the present invention, ultimately modulating the amount of cancer marker expressed. In some embodiments, siRNA and antisense therapies target RNA fusions but not the wild type transcrpts. For example, in some embodiments, nucleic acid based therapies inhibit expression of truncated PPP1CB polypeptide but not wild type PPP1CB polypeptides. For example, in some embodiments, nucleic acid therapies target the fusion junction of an RNA fusion or the start codon of the truncated PPP1CB polypeptide.

1. RNA Interference (RNAi)

In some embodiments, RNAi is utilized to inhibit RNA fusion function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments. In some embodiments, RNAi oligonucleotides are designed to target the junction region of fusion proteins.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference). An important factor in the design of siRNAs is the presence of accessible sites for siRNA binding. Bahoia et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, usually Comers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

2. Antisense

In other embodiments, fusion protein expression is modulated using antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result.

Chimeric antisense compounds of the present invention may be formed as composite structures of two or more oligonucleotides, modified oligonucleotides, oligonucleosides and/or oligonucleotide mimetics as described above.

In some embodiments, antisense compounds alter splicing of RNA fusions, thus preventing expression of truncated PPP1CB from such fusion transcripts. For example, in some embodiments, chimeric antisense moleuces that comprise a first portion that specifically binds to an RNA fusion transcript and second portion that modulates transcription or splicing (e.g., a peptide) of the RNA fusion transcript (See e.g., WO 02/38738; herein incorporated by reference in its enterity).

The present invention also includes pharmaceutical compositions and formulations that include the antisense compounds of the present invention as described below.

B. Gene Therapy

The present invention contemplates the use of any genetic manipulation for use in modulating the expression of cancer markers of the present invention. Examples of genetic manipulation include, but are not limited to, gene knockout (e.g., removing the fusion gene from the chromosome using, for example, recombination), expression of antisense constructs with or without inducible promoters, increasing expression of genes of interest (e.g., wild type PPP1CB) and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target CCL cancers that comprise YPEL5-PPP1CB or PPP1CB-YPEL5 mRNA fusions. Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies can be utilized (See e.g., U.S. Pat. Nos. 6,180, 370, 5,585,089, 6,054,297, and 5,565,332; each of which is herein incorporated by reference).

In some embodiments, the therapeutic antibodies comprise an antibody generated against a cancer marker of the present invention (e.g., YPEL5-PPP1CB or PPP1CB-YPEL5 fusions), wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, a-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using conjugation technology (See, e.g., Ghose et al., Methods Enzymol., 93:280 [1983]).

For example, in some embodiments the present invention provides immunotoxins targeted a cancer marker of the present invention (e.g., YPEL5-PPP1CB RNA fuions). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Replacement Therapy

In some embodiments, therapies that replace wild type PPP1CB are utilized. In some embodiments, therapies are genetic therapies (e.g., those described above) that incrase expression of wild type PPP1CB. In some embodiments, replacement therapies are wild type PPP1CB peptides or a function fragment thereof.

E. Pharmaceutical Compositions

The present invention further provides pharmaceutical compositions (e.g., comprising pharmaceutical agents that modulate the expression or activity of RNA fusions of embodiments of the present invention). The pharmaceutical compositions of the present invention may be administered in a number of ways depending upon whether local or systemic treatment is desired and upon the area to be treated.

Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to techniques such as, for example, bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

VII. Transgenic Animals

The present invention contemplates the generation of transgenic animals comprising an exogenous cancer marker gene (e.g., RNA fusions) of embodiments of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer (e.g., CCL).

The transgenic animals of embodiments of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

Example 1

Methods

Index Samples. Cryopreserved cell suspensions from a total of five cases with characteristic clinical and immunophenotypic features of CLL were obtained from the flow cytometry laboratories of the University of Utah/Associated Regional and University Pathologists (ARUP) and the University of Michigan. The research use of these residual specimens was approved at both institutions). The mean age of the patients was 65 y (Table 2). The samples were selected on the basis of flow cytometry-based enumeration of tumor cells such that they contained >80% of tumor cells. RNA isolation and cDNA library preparation for wholetranscriptome sequencing were performed as previously described (Kumar-Sinha et al., Nat Rev Cancer 8(7):497-511) with minor modifications.

Nomination of Candidate RNA Chimeras. Mate-pair transcriptome reads were mapped to the human genome (hg18) and RefSeq transcripts, allowing up to two mismatches, with the Illumina Genome Analyzer Pipeline software ELAND (Efficient Alignment of Nucleotide Databases). Sequence alignments were subsequently processed to nominate gene fusions, using previously described bioinformatics methodology (Maher C A, et al. (2009) Nature 458(7234):97-101).

Genomic Southern Blotting and Molecular Cloning of YPEL5/PPP1CB and Truncated PPP1CB Protein Expression. Genomic Southern blotting (Tokino T, et al. (1991) Am J Hum Genet 48(2):258-268), cloning of YPEL5/PPP1CB, and expression of truncated PPP1CB protein expression was performed according to standard procedures. FISH, Ig heavy chain variable region gene expression analysis, serine/threonine phosphatase assay, and cell proliferation and colony formation assay were performed as described below Fusion Transcript Reads in Index CLL Samples.

```
                                                   (SEQ ID NO: 1)
5'AGCCGGGGTCGAAACGCCGCGTGACTTGTAGGTGAGAG (PPP1CB)

(SEQ ID NO: 2)
3'TCCTACACTGCCTCCAAGATGGTCCAGGCTGGCATAAG (YPEL5)

(SEQ ID NO: 3)
3'GACAAGCCGCTGGCAGCCGCGGATCTCACCGCCGCTCA (PPP1CB)

(SEQ ID NO: 4)
5'GGAAACCTCCATATTCAAANAATCTCAGTAAATCTGTA (YPEL5)

(SEQ ID NO: 5)
3'GGCGCCTGTGAAACGAGTGGAGATGAGTTCTGAGCGGT (PPP1CB)

(SEQ ID NO: 6)
5'CTGAACGTGGACAGCCTCATCACCCGGCTGCTGGAGGG (YPEL5)
```

RNA isolation. RNA of white blood cells (WBC) from the CLL patients was isolated using the RNeasy kit from Qiagen. The RNAs isolated were subjected to quality check using the Agilent Bioanalyzer 2100. The samples that had RNA integrity score ≥7 were used for preparing cDNA libraries for transcriptome sequencing.

Preparation of cDNA Library for Whole-Transcriptome Sequencing. Total RNA was isolated with TRIzol (Invitrogen) according to the manufacturer's instructions. Quality assessment of RNA was performed with the Agilent Bioanalyzer 2100. Paired-end libraries (n=5) for sequencing with Illumina Genome Analyzer II were prepared according to the manufacturer's protocols using the mRNA-seq sample prep kit (Illumina) with minor modifications.

Nomination of Candidate RNA Chimeras. Mate-pair transcriptome reads were mapped to the human genome (hg18) and RefSeq transcripts, allowing up to two mismatches, with the Illumina Genome Analyzer Pipeline software ELAND (Efficient Alignment of Nucleotide Databases). Sequence alignments were subsequently processed to nominate gene fusions, using previously described bioinformatics methodology (Maher C A, et al. (2009) Nature 458(7234):97-101). In brief, mate-pairs were processed to identify any that either encompassed or spanned a fusion junction. Encompassing mate pairs refer to those in which each read aligns to an independent transcript, thereby encompassing the fusion junction. Spanning mate pairs refer to those in which one sequence read aligns to a gene and its mate spans the fusion junction. Both categories undergo a series of filtering steps to remove false positives before being merged together to generate the final chimera nominations.

Quantitative Real-Time PCR Validation. Reverse transcription. One microgram of total RNA isolated from clinical samples was used for preparation of cDNA using the SuperScript II reverse transcription kit (Life Technologies). The final product was diluted 1:5 using nuclease free water. One microliter of this diluted cDNA sample was used for quantitative real-time PCR (q real-time PCR) analyses. Primer sequences listed below.

SYBR Green assay. q real-time PCR was performed using Power SYBR Green Mastermix (Applied Biosystems) on an Applied Biosystems StepOne Plus Real-Time PCR System. All oligonucleotide primers were obtained from Integrated DNA Technologies and are listed below. Control primers were used to amplify the GAPDH housekeeping gene. All assays were performed and repeated twice, and results were plotted as average fold change relative to GAPDH.

Primers used for detecting wild-type PPP1CB, YPEL5/PPP1CB, and reciprocal fusion chimeras and by SYBR Green assay.

TABLE 1

| | |
|---|---|
| YPEL5-EX1-F1 | 5'-ATACCAGCTGAAGAGCGACAA-3' (SEQ ID NO: 7) |
| PPP1CB-EX2-R1 | 5'-AGCCTCGAACTTCTGCTTCA-3' (SEQ ID NO: 8) |
| PPP1CB-EX1-F2 | 5'-CTGAACGTGGACAGCCTCAT-3' (SEQ ID NO: 9) |
| YPEL5-EX4-R2 | 5'-GAGATGAGTTCTGAGCGGTTG-3' (SEQ ID NO: 10) |
| GAPDH F | 5'-TGCACCACCAACTGCTTAGC-3' (SEQ ID NO: 11) |
| GAPDH R | 5'-GGCATGGACTGTGGTCATGAG-3' (SEQ ID NO: 12) |

Sequence-specific quantitative real-time (TaqMan)-PCR analyses for YPEL5/PPP1CB and PPP1CB/YPEL5 chimeras. TaqMan gene expression analyses were performed using sequence-specific TaqMan probes (listed below) for YPEL5/PPP1CB and PPP1CB/YPEL5 fusion using TaqMan Q-PCR master mix from Applied Biosystems.

TaqMan Gene Expression Analyses. Custom TaqMan probes specific for YPEL5/PPP1CB and PPP1CB/YPEL5 fusion detection:

TABLE 2

| | |
|---|---|
| YPEL5/PPP1CB-F | 5'-ACCAGCTGAAGAGCGACAAG-3' (SEQ ID NO: 13) |
| YPEL5/PPP1CB-R | 5'-CACAATCTTTCCTGGACGACATC-3' (SEQ ID NO: 14) |
| YPEL5/PPP1CB-FAM | 5'-CCGCCGCTCAGGTACGA-3' (SEQ ID NO: 15) |
| PPP1CB/YPEL5-F | 5'-ACGTGGACAGCCTCATCAC-3' (SEQ ID NO: 16) |
| PPP1CB/YPEL5-R | 5'-GATATGATCAAGGAAAATTCTGCCCATT-3' (SEQ ID NO: 17) |
| PPP1CB/YPEL5-FAM | 5'-CTGCTGGAGGGTTTTT-3' (SEQ ID NO: 18) |

Sanger's Sequencing of Fusion Chimeras. YPEL5/PPP1CB and PPP1CB/YPEL5 fusion chimeras were amplified from the index and additional CLL cases using two different primer sets for YPEL5 and PPP1CB. The primers were designed to amplify across the fusion chimeras generating two different amplicons (115 bp and 325 bp) using Platinum Taq DNA Polymerase High Fidelity (Life Technologies). The PCR products were separated on a 1% agarose gel and bands excised and purified for Sanger's sequencing.

Ig Heavy Chain Variable Region Gene Expression in CLL. Total RNA was prepared from whole blood or cryopreserved WBC by using the Qiamp RNA Blood Mini Kit (Qiagen). Five microliters of RNA were used to generate random-primed cDNA by using the SuperScript III First Strand cDNA Synthesis Kit or RT-PCR (Invitrogen). cDNAs were diluted in water to achieve 2-10 ng RNA per microliter for use in PCR amplification. Previously described VH family-specific forward primers that anneal to the leader region and reverse primers that anneal to the JH region (Szankasi et al., (2010) J Mol Diagn 12(2):244-249) were used to amplify rearranged heavy chain variable regions. A primer pair that specifically matched the leader region of the VH3-21 segment was also used. Twenty-microliter reactions were assembled and contained 2 µL of diluted cDNA, leader primers(s) (0.2 µmol/L each), JH and JH-1 primer (0.2 mmol/L each), deoxynucleoside triphosphates (0.2 µmol/L each), MgCl2 (3 mmol/L), GoTaq Flexi DNA polymerase (1 unit; Promega Corp., Madison, Wis.), and GoTaq Flexi Green buffer (1x; Promega). Although VH2, VH5, VH6, and VH3-21 amplification reactions were performed with primers for each VH region multiplexed, separate reactions were assembled for the VH1, VH3, and VH4 amplification reactions. The PCR cycles were performed as follows: initial denaturation of 94° C. for 2 min, cycling denaturation at 94° C. for 20 s, annealing at 55° C. for 10 s, and extension at 72° C. for 30 s, followed by a final extension at 72° C. for 2 min and cool down to 4° C. Five microliters of each PCR amplification product were run on a 2% agarose gel and visualized by UV transillumination of ethidium bromide-stained gels. DNA sequencing analysis of PCR products was performed using BigDye terminator chemistry and the ABI3730 instrument (Applied Biosystems). Ig sequences were aligned using the VQUEST program to determine the closest matching germline VH region segment and percentage sequence identity (Brochet X, Lefranc M P, Giudicelli V (2008) IMGT/V-QUEST: The highly customized and integrated system for IG and TR standardized V-J and V-D-J sequence analysis. Nucleic Acids Res 36(Web Server issue): W503-W508).

Molecular Cloning of YPEL5/PPP1CB and Truncated PPP1CB Protein Expression. YPEL5/PPP1CB full-length fusion gene was cloned from the samples that tested positive for the RNA chimeras by qRT-PCR. Briefly, the cDNAs of the samples were subjected to PCR using the custom primers specific for the chimeric transcripts, and the amplicons were gel purified using a Qiagen gel DNA extraction kit and then cloned into a per8.0 TOPO gateway entry cloning vector (Invitrogen). The recombinants were transformed into *Escherichia coli*, and the plasmid DNAs for selected clones were isolated and sequence verified. The full-length wild-type PPP1CB (Open Biosystems) and YPEL5/PPP1CB fusion genes were cloned into p.c.DNA 3.1 (+) mammalian expression vector (Invitrogen) between BamH1 and Xba1 restriction site. FLAG sequences were artificially introduced at the C-terminal end of the gene by PCR. Sequenceverified clones were transfected into HEK 293 cells using PolyJet (SignaGen Laboratories). The lysates were prepared from these cells, 48 h after transfection using RIPA buffer containing 50 mM Tris-HCl (pH 7.4), 1% Nonidet P-40, 0.25% Na-deoxycholate, 150 mM NaCl, 1 mM PMSF, 1 mM EDTA, 1 mM Na3V04, 1 mM NaF, and 0.1% SDS. The samples were incubated on ice for 30 min followed by centrifugation at 11,200×g for 15 min. The supernatants collected were estimated for protein content using a protein BCA assay kit (Pierce protein research products). Fifty micrograms of protein extract were separated on high-resolution SDS/PAGE using Mes SDS running buffer and analyzed for expression of proteins by Western blotting using monoclonal ANTI-FLAG M2 (clone M2) antibody (Sigma).

Fluorescence in Situ Hybridization. BAC clones were used to generate the dual-color break-apart FISH probes for PPP1CB (RP11-1079D1-5' and RP11-984I213') and YPEL5 (RP11-104E4 5' and RP11-136A10-3'). Two hundred milliliters overnight cultures for each BAC clone were grown in LB medium containing 12.5 µg/mL of chloramphenicol at 37° C. for 14-16 h with constant shaking DNA was prepared using a Qiagen midiprep kit using Qiatip-100 according to the protocol provided by the manufacturer. All FISH probes were prepared by nick translation labeling using modified nucleotides conjugated with biotin or digoxigenin using biotin nick translation mix (11745824910; Roche) for 3' probes, digoxigenin nick translation mix (11745816910; Roche) for 5' probes. Probe DNA was precipitated and dissolved in hybridization mixture containing 50% (wt/vol) formamide, 2×SSC, 10% (wt/vol) dextran sulfate, and 1% Denhardt's solution. Approximately 200 ng of each labeled probe was used for hybridization. Fluorescent signals were detected with Streptavidin Alexa Fluor 594 (S-32356; Invitrogen) and anti-digoxigenn fluorescein Fab fragments (11207741910; Roche) for red and green colors, respectively. All clones were tested on normal human metaphase chromosomes to validate map position. FISH scoring was performed by an experienced cytogeneticist (N.P.). Fluorescent images were captured using a high-resolution CCD camera controlled by ISIS image processing software (Metasystems).

Southern Blotting of Genomic DNA. Five micrograms of genomic DNA from CLL samples positive for fusions by qRT-PCR and benign hyperplasias were digested overnight at 37° C. with appropriate restriction endonucleases. The digested DNA was then separated on 1% agarose gel along with a 1-kb DNA ladder from New England labs 0 V for 14 h. The gel was then stained with ethidium bromide gel, documented, and irradiated for 30 s on a UV box to nick the DNA fragments for better transfer. The gel was washed with denaturing solution containing 2% NaOH and 8.8% NaCl for 30 min, then placed in deionized water for a few minutes before transfer into a neutralizing solution containing 6% Tris and 8.8% NaCl for 10 min. The DNA on the gel were then transferred to Zeta Probe nylon blotting membranes (Bio-Rad) by capillary electrophoresis using 8×SSC containing 7% NaCl and 3.5% sodium citrate at room temperature overnight. Transferred DNA were UV cross-linked at 1,200 J and then baked at 80° C. in a vacuum oven for 1 h. After prehybridizing at 42° C. overnight in a water bath with a prehybridization solution[50% (wt/vol) deionized formamide, 30% 20×SSC, 10% (wt/vol) 50×Denhardt's solution, 0.5% SDS, 1% 10 mg/mL Herring testes DNA], the membrane was then hybridized with the genomic probes containing 32P in a hybridization solution containing 20% 50% wt/vol dextran sulfate, 40% deionized formamide, 20% 20×SSC, 0.35% 2 M Tris (pH 7.4), 1.6% 50×Denhardt's solution, and 1% 10 mg/mL Herring testes DNA overnight at 42° C. The membrane was then washed with 2×SSC at 55° C. twice, dried, and exposed to a Kodak Biomax film (Sigma-Aldrich) at −80° C. overnight and developed the next day.

YPEL5 probe 1 (500 bp).
(SEQ ID NO: 19)
GCTCCGCCAGCTTCGGGCTGCGGCCTTCCCTCCGCTTGCAGTC

GGGAGGGTGGGCGTGCCCTTGCAACCCCTTTCCTGTACCTTCT

CTGCAGGTAGATGGGACAAATGAGTGTCCGGATCAGCGGGAGT

GGGAAATTGAAATACTACAAAGATCTGTTTAATCCTGATACCA

ACTAATCTCCCTTTCAAGGGAGAGTCTGGGAAGCTGTACAGCT

CATTTATTTTAAACTTTTTCTGTTTACAGAGATCTGTTGGTA

ATCTGAGGATTTTTATTCTACGTCGTCTTGACAGATGGAAAAC

CTGAAGTAACTTCGGGCTAACCTTGTGTTTTTGGAAAATTAGT

AGACTTGGTGGTGAAGAAACTGGGAGGAGTAGGATATTAGCTA

ACTTTGCATAGCCACATATAGAGCGTCGCAGCTGCATTCCACC

AAAGAGGAACCAAAAGGCCTGTGGTGTTCCCAGGGTACATATT

CATGCCAGAAGTGAAGTGCTTTGGTGA

YPEL5 probe 2 (500 bp).
(SEQ ID NO: 20)
GTAAGAAGTAAAGTACAAAGAATTTAGAATAGTTTCTCTAGAA

GCTTATAACTTAATCAAAAGTCGTGGACAAAGTCGAGCAATAA

TTTTAGCAAGTTATGAGACGTTAGTAAAATATATGTAGCTTGG

AAAATAATGTTACCTGGTTGGATCATTGCGAACTTTTCTCTAG

ACTAATTTCCCTTTTCTGTTTTCTATTTAAGTAATGAGAAAAA

TAAACAGGTTTAGAAAAAAGTGAAAGGAAATAAGGCCAAAAAT

TATGAAAAGAAGTAATTAAAGCAGCTACTACCCTCTGAAAAAC

AGTCCACGAGACATGAAGGTAGTCCTAGGTATATGTGTGCCTA

AAATATCATTCTAGGTTTAATGGTGAATAACTATAGAGATCAG

TGTCAGTTTTAAGATAATCCTGTGTAGTAATGTCAGTGTAATG

CAGGAACTGAACCTTAGCTAGACCTGAAGTTGCTACTTGACAC

TTGAGTCGGGAAGCCAGACAGGTAAAT

YPEL5 probe 2
(SEQ ID NO: 21)
R1-ACCCCCGGGTGGGCTCACCCGGC

YPEL5 probe 2
(SEQ ID NO: 22)
F1-GACTCGGGTGGCCGAGGGCTTC

PPP1CB probe 1 (525 bp).
(SEQ ID NO: 23)
CGCACCGCGCGCCTGCGCGGAGAGCTGCGTGACGCGGCGG

GCGCAAGGGACGTGCGGAGTGAGTGGCGCTGCGGGTGGGGC

CGTCGGCGGCGCTGGTGAGCTTTGCGGAGCTGGGCGGTGCC

GAGGAGGAGGAGGTGGCGGCCTGGGTCTGACGCGGCCCTGT

TCGAGGGGCCTCTCTTGTTTATTTATTTATTTTCCGTGGG

TGCCTCCGAGTGTGCGCGCGCTCTCGCTACCCGGCGGGGAG

GGGGTGGGGGAGGGCCCGGGAAAAGGGGGAGTTGGAGCCG

GGGTCGAAACGCCGCGTGACTTGTAGGTGAGAGAACGCCGA

GCCGTCGCCGCAGCCTCCGCCGCCGAGAAGCCCTTGTTCCC

GCTGCTGGGAAGGAGAGTCTGTGCCGACAAGATGGCGGACG

GGGAGCTGAACGTGGACAGCCTCATCACCCGGCTGCTGGAG

GGTGAGTGCGCGCCTGGCCGCGGGACAGAGGGAGGTCGGGC

ACCGCCGCCGACCCCTGCGTCCCCGTCTGCCGCC

PPP1CB probe 1
(SEQ ID NO: 24)
F-ATTGCCCTTGGCTGCCTCCGATTGTCG

PPP1CB probe 1
(SEQ ID NO: 25)
R-ACAGTACATATGCAATCGCTGGACGGCGG

PPP1CB probe 2 (693 bp).
(SEQ ID NO: 26)
AAGGAATAGCTTTTGTGAATTTCGGACTCCCAACTACTAGAA

TTATGTGAATCCTGAATGATAATCAGATGTTTACTCAGTTAA

GTGTTTACTCAAATATTAATAAGTATTGATACATTGGGATGC

CATCTTATATAATGATTAACGACACAGATTCTGGGTGTATTT

CAGCCCCAGTTTCTTCTGCATATATGATAGTAAGTGCCTTCA

AACAATTCTTGACACATTAAAGGTCAGAAAATGTTAGCCGTC

ATTATTGCTTAGTACAAACCTGAGCTAGGAAATACTAACAGA

GAGCTCTTTGTGCCACTGAGTCCTGGAACTTCCCCATACTAA

TTTTGAGAAGGCTTTCTTGTAAGTATGTGACAGATACTGTTT

CCTCCACTTTCTGTTTATTGCATATAACCACTATTCTTGTAT

GTAAGTACGTATAACAGTTTCTTTACTATTCCCATTATTCAG

CGTTTATAATCTGGTTTGACATATCAGTGTTGGTGCTGAGAG

GGAAAGGTATTTCTAGGTAGGATAAAATGGTGAAAAGTGATT

TAACACTGTTGTATGCTTGCTTTTGGCCAGGAACTATAGGGC

AGTGTATCTTAAACTTTGAGTCTTGAGACCCTCTTACACTCA

AATTCTCCATATATGTAAAGAATTGAAAACGAGCTTTTATTT

ATGTGAGGTATTTAACAATAT

PPP1CB probe 2
(SEQ ID NO: 27)
F-TGCAAACCTGTCAGTGAGAAAGAGTGAGGTCTG

PPP1CB probe 2
(SEQ ID NO: 28)
R-T CTCAGCACCAACACTGATATGTCAAACCAG

PPP1CB probe 3 (489 bp).
(SEQ ID NO: 29)
TCAGGTGATCCACCCACCTCAACCTCCCAAGGTGCTGGGAT

TACAGGCATGAGCCACCGTGCCCGGCCCTGAAATCTTTTAA

GTCTCTTTGGCTACTAGGCCCCAGGTTGGTCACAGGACAGC

AAAAAACAGGACTGCATTTCATCAACAGCAGACTTGAGGAG

CATCATCAGGAACCAGTAACAATGAAAATAGAAGTCAGAGA

TCATAGAATAACATTATTTTAAACCATGGGACCAAATAGGG

TAATTTGCTGCCTGTGTGACTTTTCTGATTTTTAAAGTATG

GGCATGACTCTTTTTGAAAGATTATTATGAGTAAATTTTAG

AAAACTGACTGTTTTATTTATCGTTTGTCAGTACGAGGATG

TCGTCCAGGAAAGATTGTGCAGATGACTGAAGCAGAAGTTC

-continued

```
GAGGCTTATGTATCAAGTCTCGGGAGATCTTTCTCAGCCAG

CCTATTCTTTTGGAATTGGAAGCACCGCTGAAAATTTG
```

PPP1CB probe 3
(SEQ ID NO: 30)
```
F-AGTCTCTTTGGCTACTAGGCCCCAGG
```

PPP1CB probe 3
(SEQ ID NO: 31)
```
R-TACATACCACAAATTTTCAGCGGTGCTTCC
```

Figure 6:
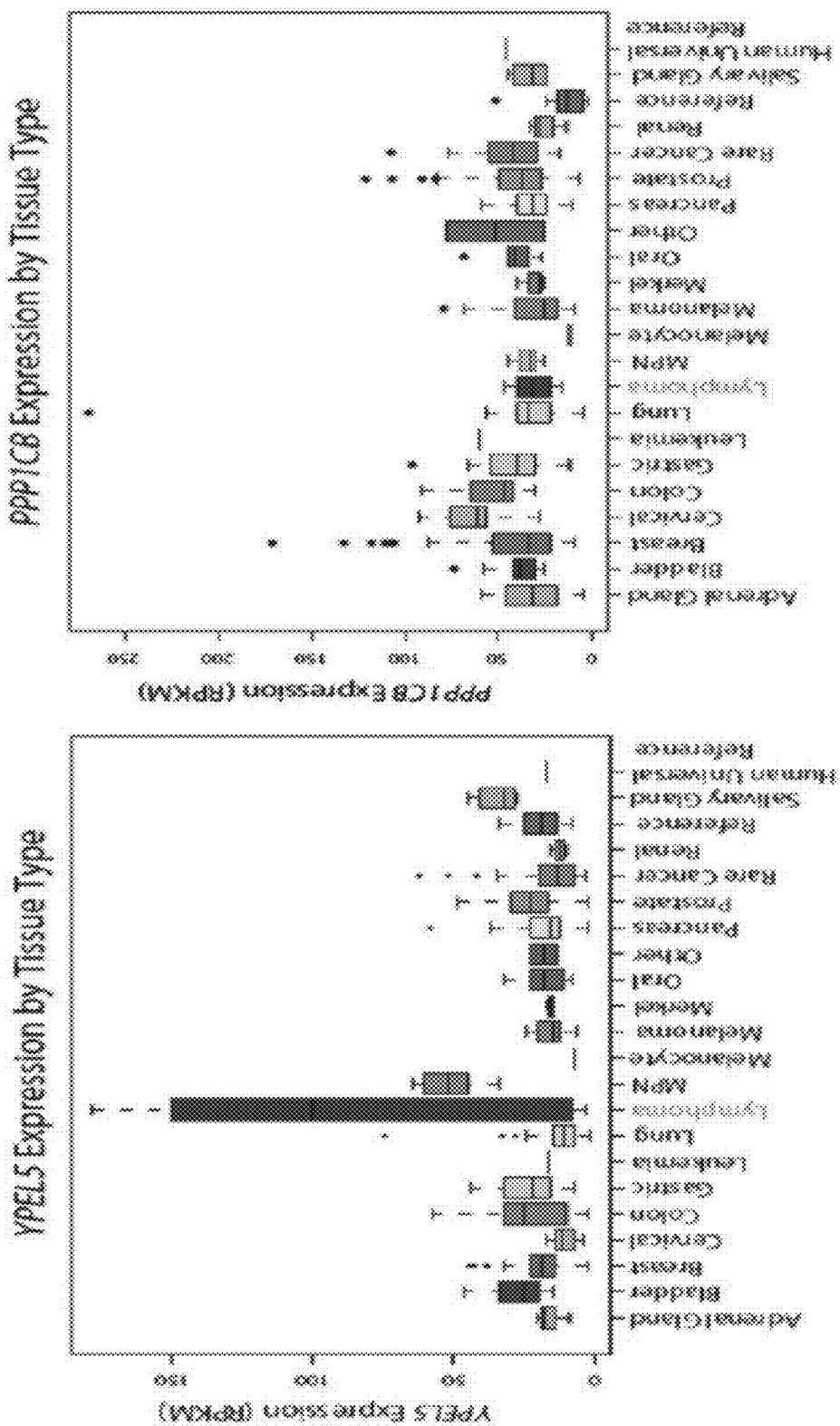
FIG. 6 shows Lymphoma-specific high-level expression of YPEL5.

Analysis of YPEL5 and PPP1CB Loci for Evidence of Genomic Rearrangements. Whole-genome sequencing and analysis of CLL genomic library construction for massively parallel paired-end sequencing was performed as previously described (Bentley D R, et al. (2008) Accurate whole human genome sequencing using reversible terminator chemistry. Nature 456(7218):53-59). Mate-pair sequencing was performed on genomic DNA isolated from two index samples (C41, E84) on an Illumina GAII analyzer according to standard Illumina protocols (Chen W, et al. (2008) Genome Res 18(7):1143-1149). Mapping was performed using Bowtie (Langmead et al., (2009) Genome Biol 10(3):R25) and analyzed using VAMP (Kondo A, et al. (2010) Blood 116(7):1124-1131). Sequencing data were aligned to the human reference genome (GRCh37). The resulting libraries were composed of high-quality ~5-kb fragments giving 8.1- and 15.3-fold fragment coverage per diploid allele for SI_3560/C41 and SI_3562/E84, respectively, and thus an expectation of sufficient sensitivity for detecting most structural genome alterations. Attempts to detect such an alteration at YPEL5 and PPP1 CB were first performed in a blinded genome-wide fashion according to established methods that seek clusters of anomalously mapping pairs consistent with a structural alteration (Kondo A, et al. (2010) Blood 116(7):1124-1131). This revealed no anomalies in or around YPEL5 or PPP1CB. Instead, a large number of normally mapping pairs consistent with diploid genome content were detected (FIGS. 6A and B). To minimize the likelihood of false-negative results, the PPP1CB and YPEL5 exons flanking the anomalous splice junctions in chimeric transcripts were correlated back to genome coordinates to identify genome segments where a putative translocation junction would need to have occurred, including sufficient flanking sequence for locating mate-pairs crossing the junction (hg19 Chr2:28,969,042-29,005,717 and Chr2:30,363,928-30,385,494 for PPP1CB and YPEL5, respectively). All mate-pairs were identified for which at least one read of the pair could map to one of these regions. To exhaustively reveal any evidence of genomic fusion sequences in this analysis, all possible mappings with up to three mismatches were accepted to include mate-pairs in repetitive elements that might have been filtered in the blinded analysis. Despite this, no mate-pairs clusters were identified that connected the candidate genomic regions in a manner consistent with a translocation junction.

Expression and Purification of Full-Length and Truncated PPP1CB in E. coli with GST tag. PPP1CB wild-type or truncated coding sequences were PCR amplified and cloned into BamH1 and Sal1 in pGEX 4T1 (GE Healthcare Biosciences) prokaryotic expression vector containing sequences for N-terminal GST. The sequence-verified clones were transformed to E. coli BL21. The recombinant fulllength PPP1CB (PP-FL) or truncated (PP-Tr) proteins were affinity purified using 0.2 mL of glutathione-Sepharose resin. The bound GST fusion proteins were eluted using 10 mM reduced glutathione. The eluates were dialyzed against dialysis buffer [20 mM Tris.HCl (pH 7.5), 20 mM KCl, 50% glycerol] to remove excess glutathione. A fraction of the purified proteins was run on SDS/PAGE and analyzed by Coomassie blue staining and Western blotting using PPP1CB antibody.

Serine/Threonine Phosphatase Assay. Phosphatase assays for PP-FL or PP-Tr proteins were performed using Ser/Thr phosphatase assay kit 1 (catalog no. 17-127 from Upstate Cell Signaling Solutions) according to the manufacturer's protocol with slight modifications (Kondo A, et al. (2010) Blood 116(7):1124-1131). Briefly, PP-FL or PP-Tr proteins were incubated with or without 10 µL of phospho peptides (1 mg/mL) for 30 min at room temperature in a 96-well plate with gentle shaking on a platform shaker. After incubation, 10 µL of malachite green solution (40% of malachite green dye solution, 40% phosphate free deionized water, 20% 7.5% ammonium molybdate, and 1.5% 11% Tween 20) was added to both sample and series of standard wells and allowed for color development for 15 min at room temperature. The plate was then read at 650 nm.

Cell Proliferation Assay. Cell proliferation assay was performed by using water-soluble tetrazolium-1 (WST-1) procured from Roche Applied Sciences according to the manufacturer's protocol (Kondo A, et al. (2010) Blood 116(7):1124-1131). Briefly, equal numbers of cells were plated in 96-well plates with growth media, and 10 µL of WST-1 reagent was added at different time intervals (0, 12, 36, and 48 h). After addition of WST-1 reagent, the plates were incubated at 37° C. in an incubator with 5% CO2 for 2 h. According to the cleavage of the tetrazolium salt WST-1 by mitochondrial dehydrogenases in viable cells, the intensities of the color developed in each well were determined by measuring the absorbance at 600 nm. The assay was performed in triplicate for all of the samples at each time point.

Colony Formation Assays for Human Cells. Colony-forming cell assays were performed using MethoCult H4230 methylcellulosebased media obtained from Stem Cell Technologies. The experiments were carried out by following the instructions mentioned in the manufacturer's protocol (Kondo A, et al. (2010) Blood 116(7):1124-1131). Cell suspensions were prepared at 10× concentration (2,000 cells per mL) in growth media. Of the above suspension, 0.4 mL was mixed with 4 mL of MethoCult media. The tubes were mixed well by vortexing and allowed to stand for 5 min. Of this mixture, 1.1 mL was carefully plated in 35-mm dishes in triplicates. The plates were then incubated at 37° C. in 5% CO2 with 95% humidity for 14-16 d. After 14 d, 250 µL of 5 mg/mL iodonitrotetrazolium salt solution was layered on the top of the plates and left overnight.

The viable cells which form colonies take up the salt and metabolize them to give a dark brown stain. The numbers of colonies were counted under microscope.

Results

Chimera Candidates for CLL. Using a previously described analysis pipeline for chimera discovery (Maher C A, et al. (2009) Nature 458(7234):97-101; Maher C A, et al. (2009) Proc Natl Acad Sci USA 106(30):12353-12358), a total of nine RNA chimeras were identifed in seven cases of CLL (Table 3). Of these candidates, six chimeras represented read-throughs of adjacent genes, two represented chimeras resulting from juxtaposition of transcripts encoded by genes on different chromosomes, and one represented chimeric transcripts from noncontiguous genes within the same chromosome (Table 3). The chimera representing fusion of two discontinuous gene transcripts was a reciprocal chimeric fusion between YPEL5 and PPP1CB genes (average read count n=3).

The fusion between the YPEL5 and PPP1CB was further analyzed based on its reciprocal nature, its recurrence (2/7), and exclusive identification in the CLLs compared with more than 500 other tumors within the compendium of tumors investigated by paired-end whole-transcriptome sequencing (PETS). Accordingly, a q real-time PCR was performed using cDNA prepared from the index clinical specimens of CLL and the results of PETS was confirmed in the index cases (FIGS. 1 B and C).

To characterize the complete YPEL5/PPP1CB and reciprocal fusion transcripts, Sanger sequencing was performed of RT-PCR products obtained from cDNA prepared from the two index (discovery) CLL samples and an additional eight cases of clinically and phenotypically typical CLL in which the YPEL5/PPP1CB fusion was detected by q real-time PCR. Direct Sanger sequencing of the PCR products from two independent PCR reactions (115 bp and 325 bp) (FIG. 5C) with different primer sets confirmed juxtaposition of sequences derived from YPEL5 and PPP1CB in both YPEL5/PPP1CB and the reciprocal PPP1CB/YPEL5 (FIG. 1D) configurations in all six cases of CLL.

Figure 7:
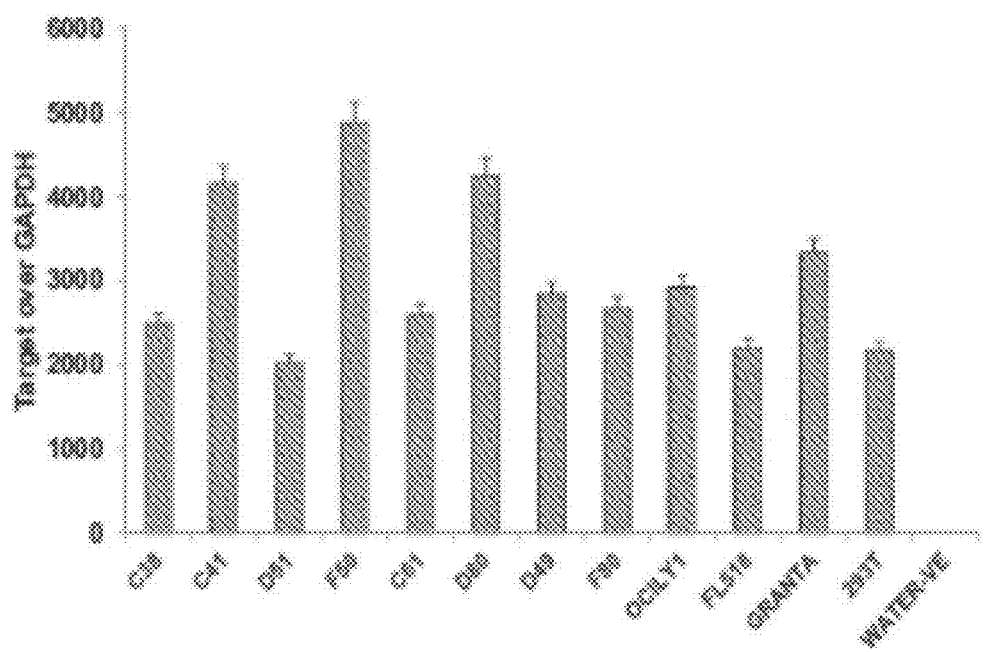
FIG. 7 shows Q real-time PCR analysis for the expression of wild-type PPP1CB.

Analysis of the expression of YPEL5 and PPP1CB within the compendium of RNA seq data generated from >500 independent samples representing different types of cancer revealed significantly higher levels of YPEL5 expression in the CLLs, indicating a lineage or tissue-specific promoter activation, whereas PPP1CB levels observed in CLL were comparable to those observed across all other tumor samples and cell lines (FIG. 7).

Figure 5:
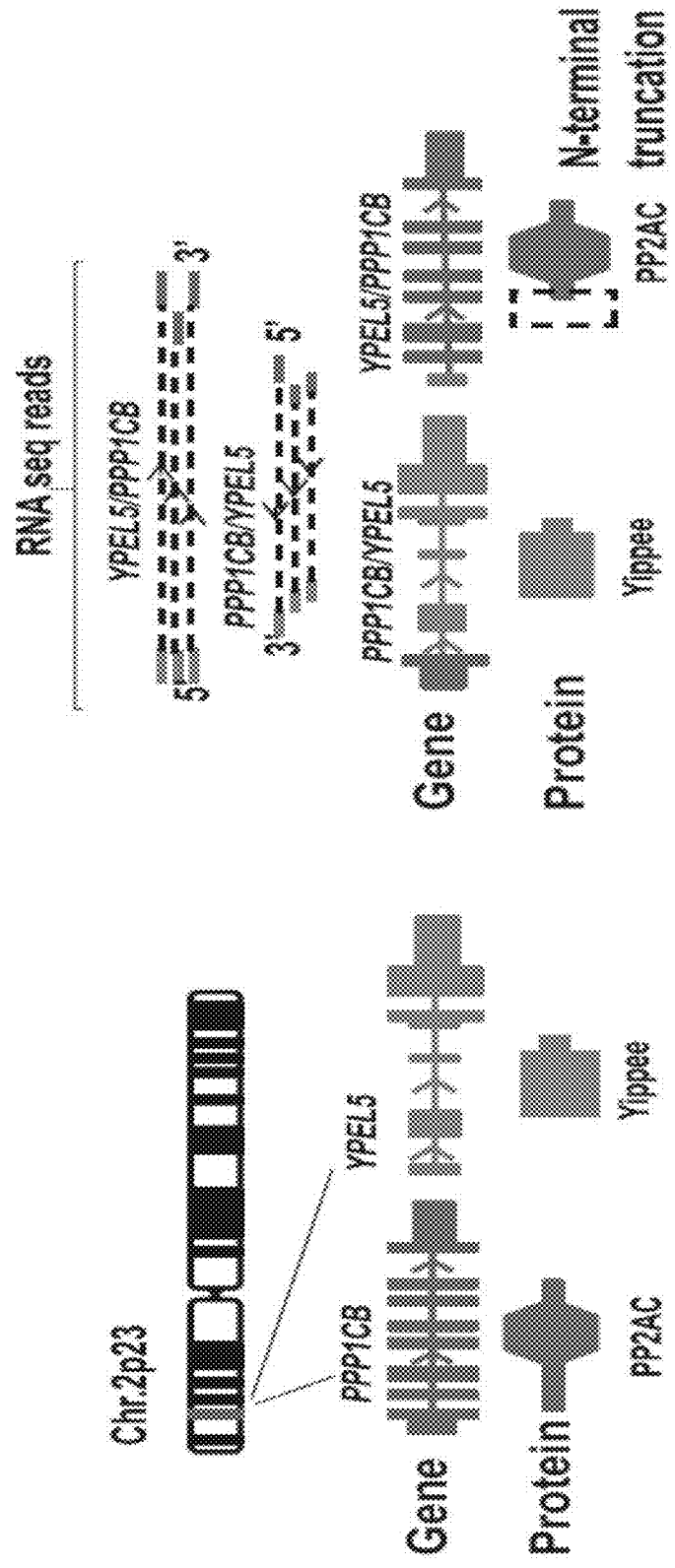
FIG. 5 shows (A) RNAseq reads representing the relevant fragments that map across YPEL5 and PPP1CB genes to indicate the occurrence of chimeric fusions. (B) Genomic map showing the approximate distance and genes spanning between PPP1CB and YPEL5 at position 2p23 of the chromosome. (C) Agarose gel electrophoresis of PCR amplicons obtained using two different YPEL5 and PPP1 CB primers designed to amplify across the chimeric fusion transcripts.
Figure 5:
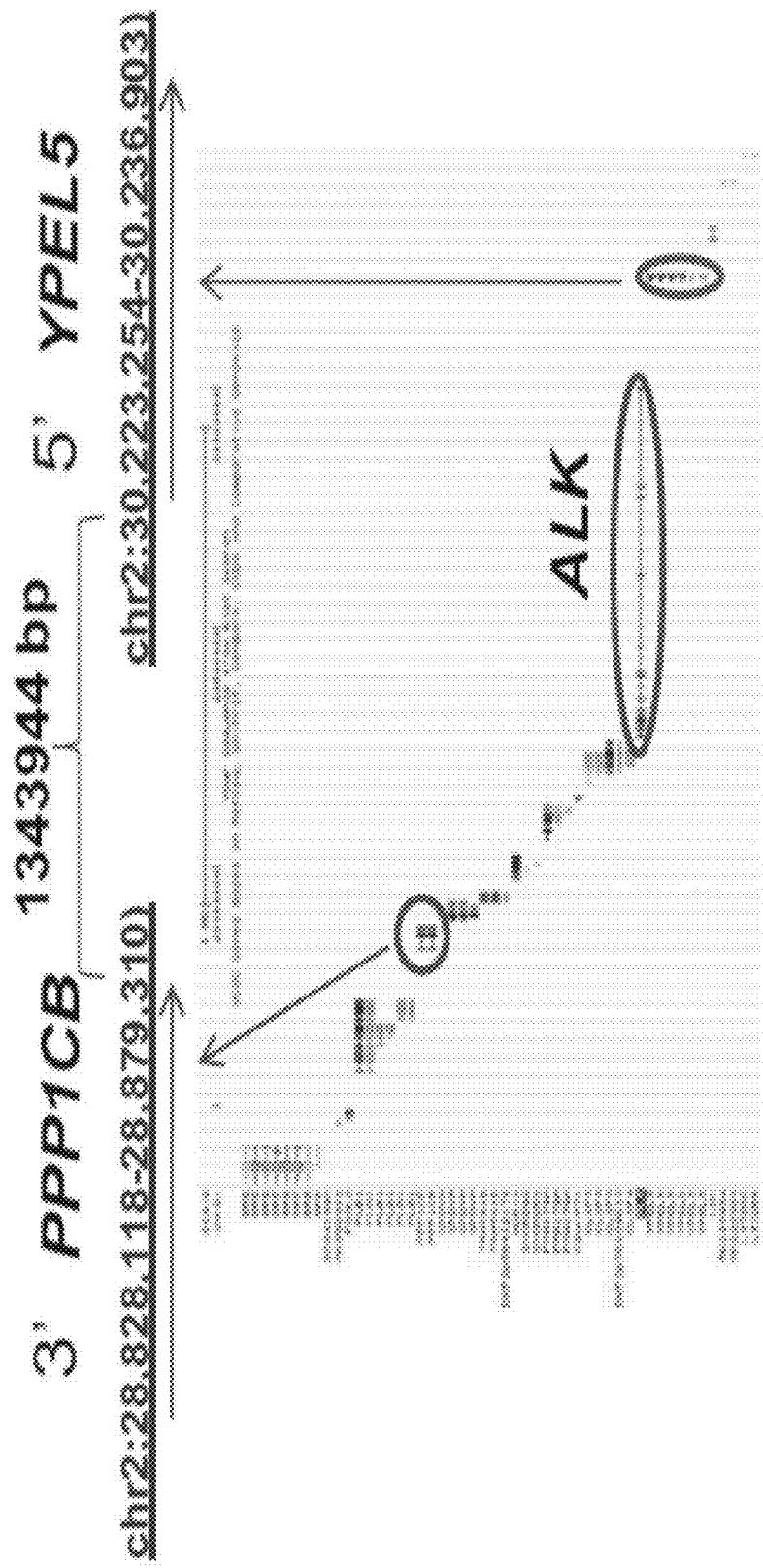
Figure 5:
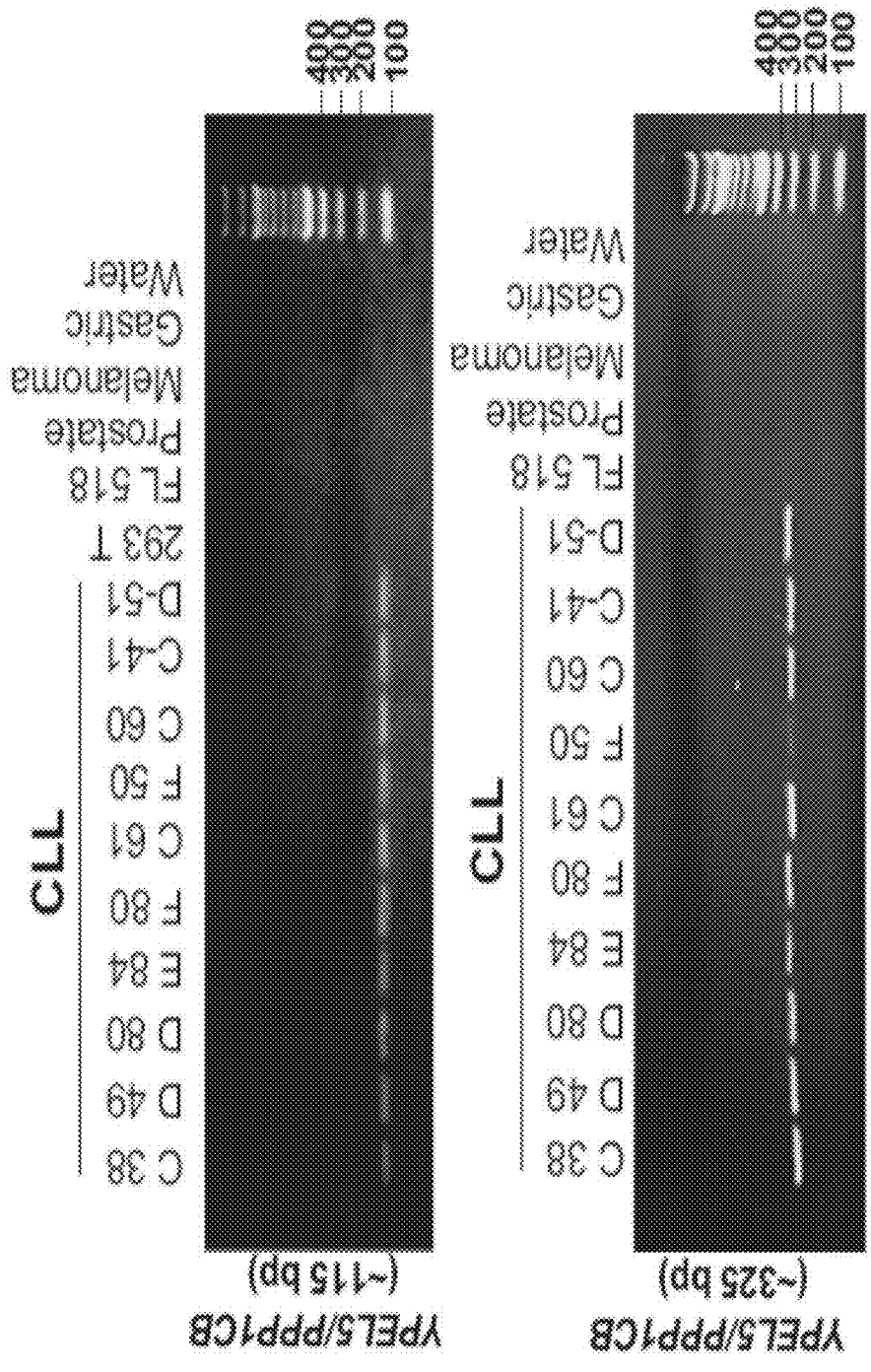

In the YPEL5/PPP1CB fusion, the noncoding exon 1 of YPEL5 is juxtaposed to exon 2 of PPP1CB. This juxtaposition results in loss of exon 1 of PPP1CB (containing the initiation codon) and utilization of an alternative initiation codon from exon 2, whereas YPEL5 contributes only 5' untranslated sequences (FIG. 1A and FIG. 5A). This aberration leads to generation of a protein in which the first 28 amino acid residues are lost from the wild-type PPP1CB protein, leading to a 299-aa residue truncated protein composed of residue 29 to residue 327. The N-terminally truncated protein retains an intact PP2Ac phosphatase domain (FIG. 5A).

In the reciprocal PPP1CB/YPEL5 fusion, exon 1 of PPP1CB is juxtaposed to exon 3 of YPEL5, generating a fusion transcript that encodes the full-length wild-type YPEL5 protein without a coding contribution from PPP1CB (FIG. 5A).

Figure 2:
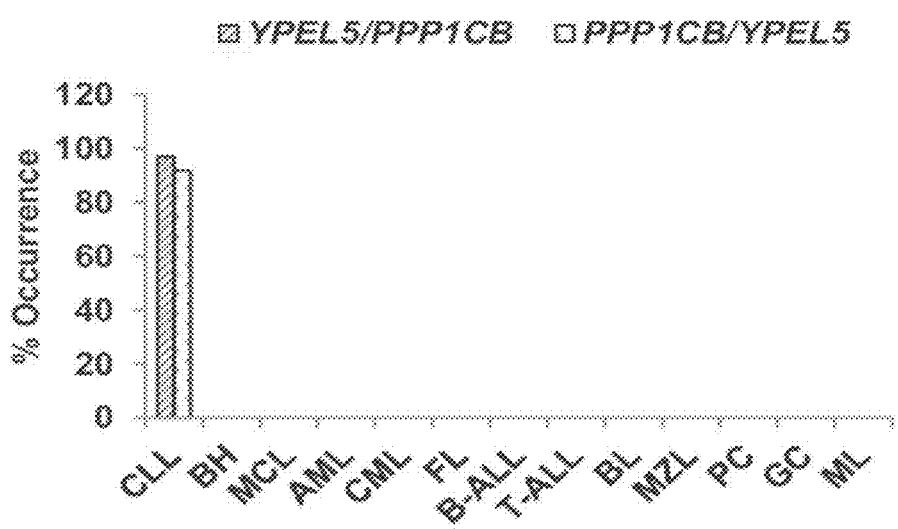
FIG. 2 shows YPEL5/PPP1CB and PPP1CB/YPEL5 fusions in CLL. (A) Extent of YPEL5/PPP1CB and PPP1CB/YPEL5 expression in CLL, benign hyperplasias, other lymphoid malignancies, and solid tumors. (B) TaqMan q real-time PCR analyses for fusion genes in germinal center B cells and naïve, memory B cells vs. CLL. (C) Somatic acquisition of YPEL5/PPP1CB and PPP1CB/YPEL5 in CLL. TaqMan q real-time PCR validation. (D) Expression of PPP1 CB full-length (PP-FL) and truncated protein (PP-Tr) in HEK 293 cells.
Figure 2:
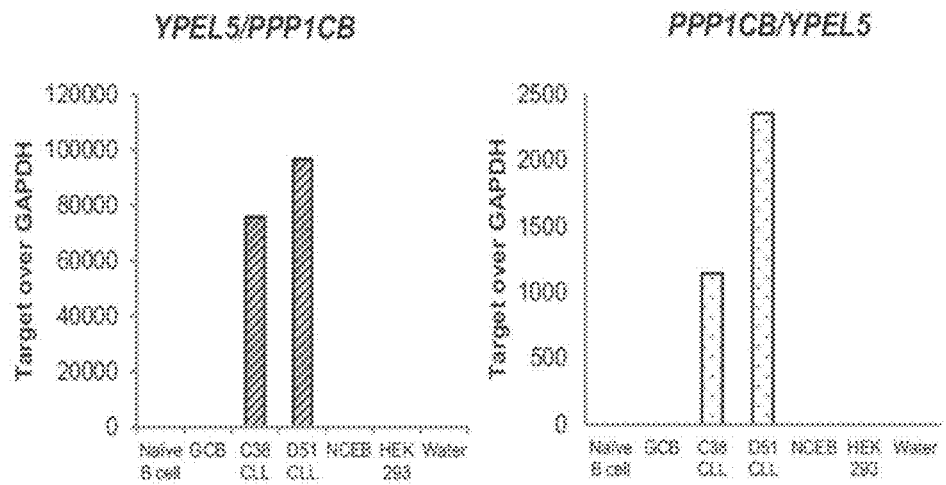
Figure 2:
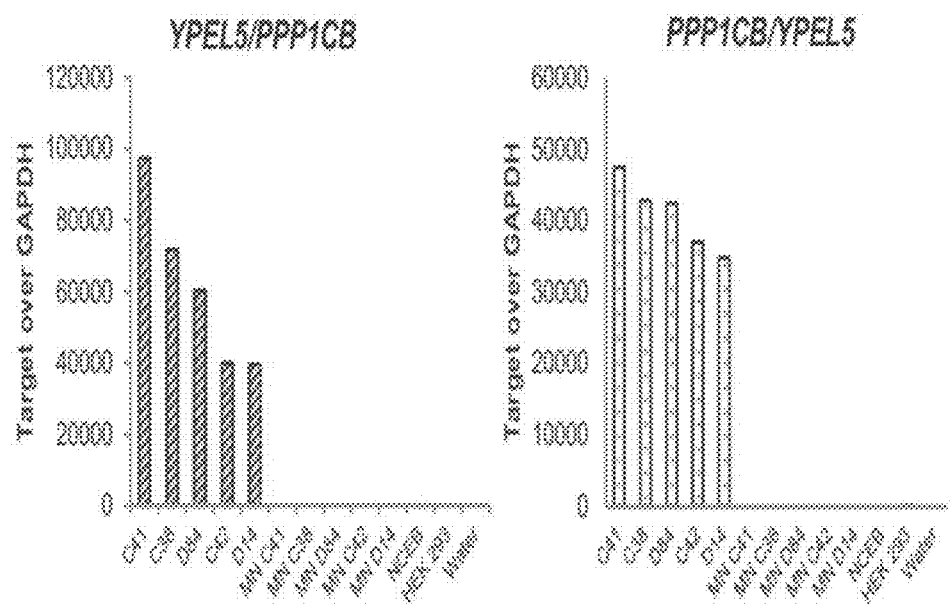
Figure 2:
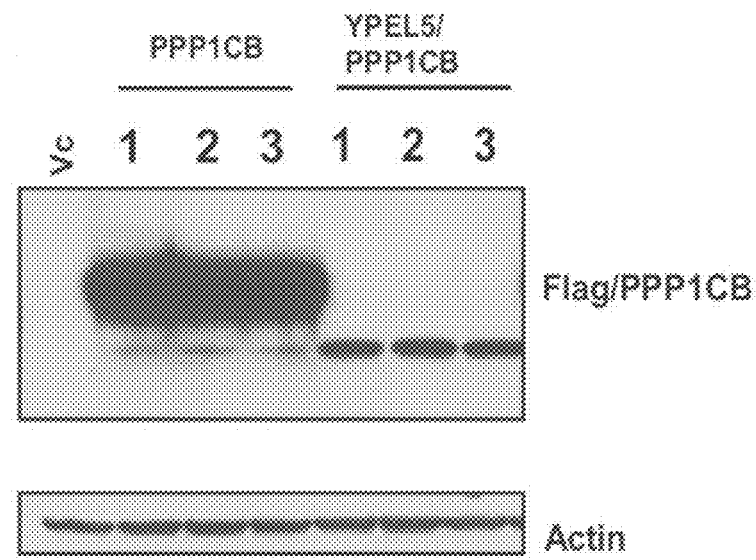

Validation of YPEL5/PPP1CB and Reciprocal Fusion in Independent Cases of CLL. Independent conventional gel-based, SYBR Green I, and fusion-specific hydrolysis (TaqMan)-based q real-time PCR assays targeting the YPEL5/PPP1CB and PPP1CB/YPEL5 fusions were designed and used to investigate 103 cases of CLL, as well as 5 benign lymph node hyperplasias and purified lymphocyte subpopulations, germinal center B cells, naïve B cells, memory B cells, and T cells purified from hyperplastic tonsils. Additionally, a total of 135 primary samples of a diverse spectrum of primary human cancers including mantle cell lymphoma (n=43), acute myelogenous leukemia (n=17), chronic myelogenous leukemia (n=10), follicular lymphoma (FL) (n=6), precursor B-cell acute lymphoblastic leukemia (n=5), precursor T-cell acute lymphoblastic leukemia (n=5), Burkitt lymphoma (n=5), marginal zone lymphoma (n=4), prostate carcinoma (n=14), gastric carcinoma (n=13), and malignant melanoma (n=13) were investigated. In addition, a total of 12 cell lines, including mantle cell lymphoma (n=1), FL/diffuse large B-cell lymphoma (n=3), acute myeloid leukemia, (n=5), mast cell leukemia (n=1), prolymphocytoid B-cell chronic lymphocytic leukemia (n=1), and epithelial cancer (n=1), were tested. Only the primary CLL specimens showed PCR evidence for the reciprocal fusion (FIGS. 2 A and B).

To establish that the YPEL5/PPP1CB and reciprocal chimeras were expressed preferentially in the tumor cells, paired samples (n=5) comparing CLL cells immunoaffinity enriched using B cell-specific anti-CD19 conjugated beads to nonmalignant granulocytes obtained by immunoaffinity enrichment with an anti-CD13/33 mixture were investigated. In all cases, only the B-cell fractions containing CLL tumor cells revealed YPEL5/PPP1CB and reciprocal chimeras by q real-time PCR, whereas the granulocyte-cell fractions were negative (FIG. 2C). Further, to know whether the reciprocal chimeras affect the expression of wild-type PPP1CB in chimera-positive patient samples, SYBR green-based q real-time PCR was performed to measure the levels of PPP1CB wild-type transcripts. The results show that there was expression of wild-type PPP1CB at comparable levels to controls that were negative for chimeras (FIG. 7).

Figure 3:
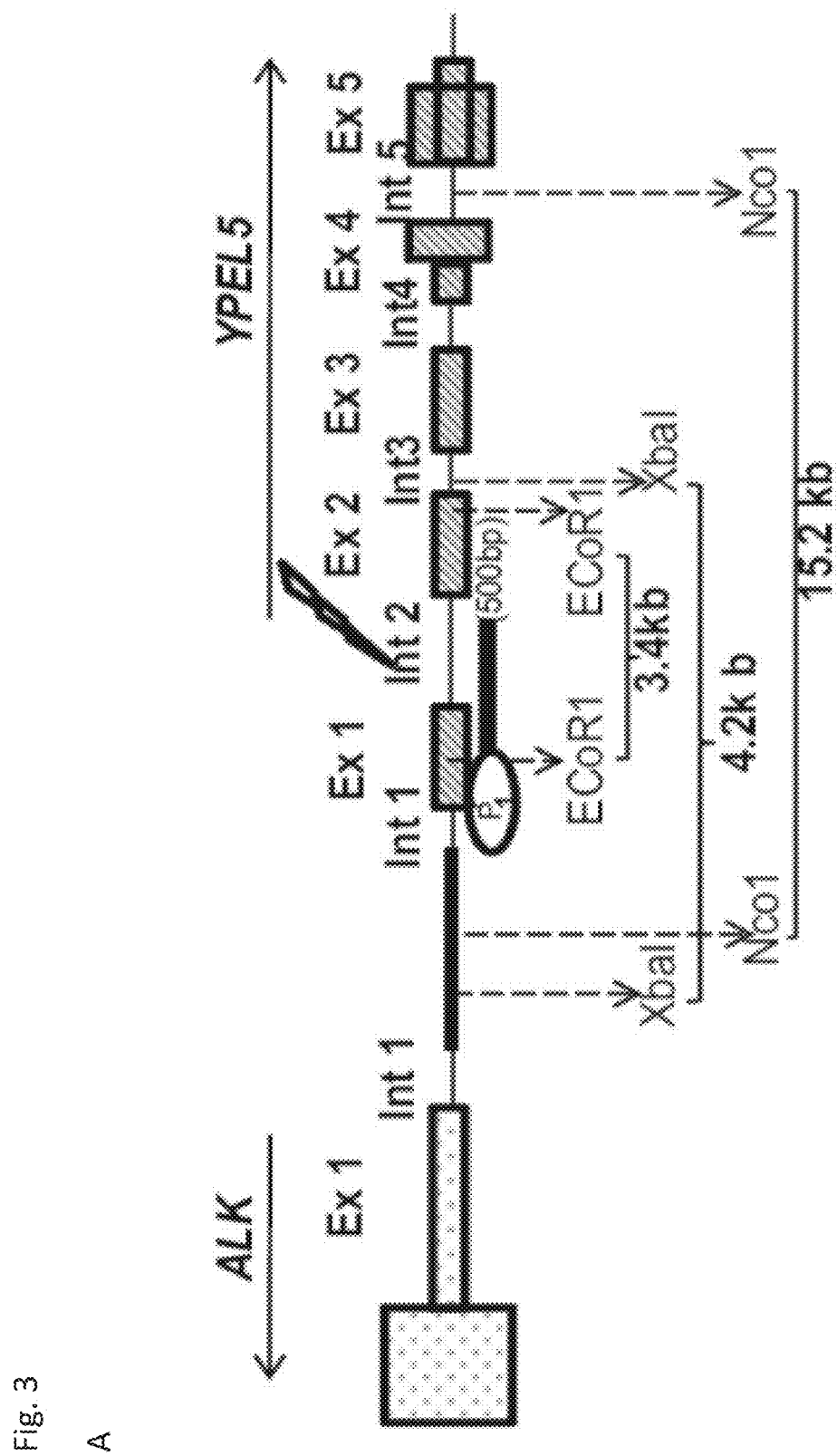
FIG. 3 shows YPEL5/PPP1CB and PPP1CB/B YPEL5 fusions in CLL. (A) Restriction sites map depicting the sites targeted in intron 2 of YPEL5 by different restriction enzymes. (B) Southern blotting analyses of CLL and benign hyperplasias (normal lymph node). (C) Whole-genome mate-pair sequencing results. (D) Genomic organization and FISH validation of PPP1CB and YPEL5 in CLL.
Figure 3:
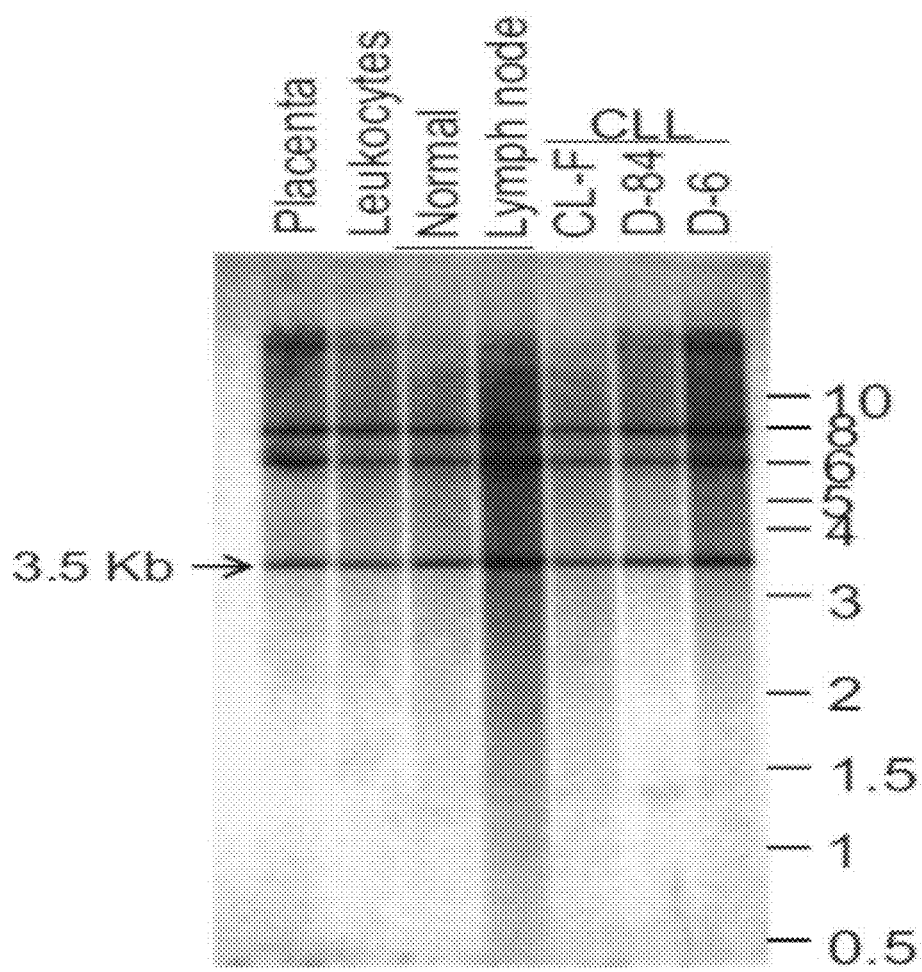
Figure 3:
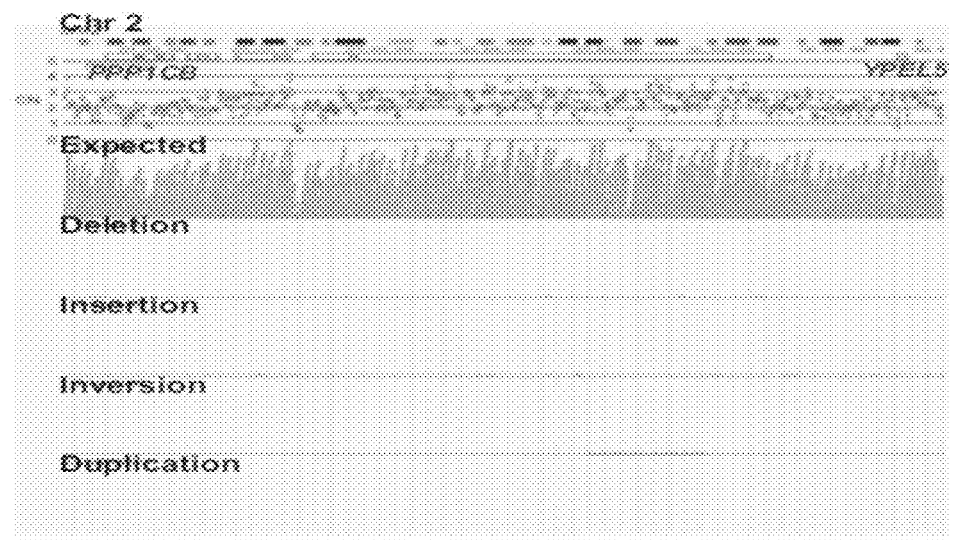
Figure 3:
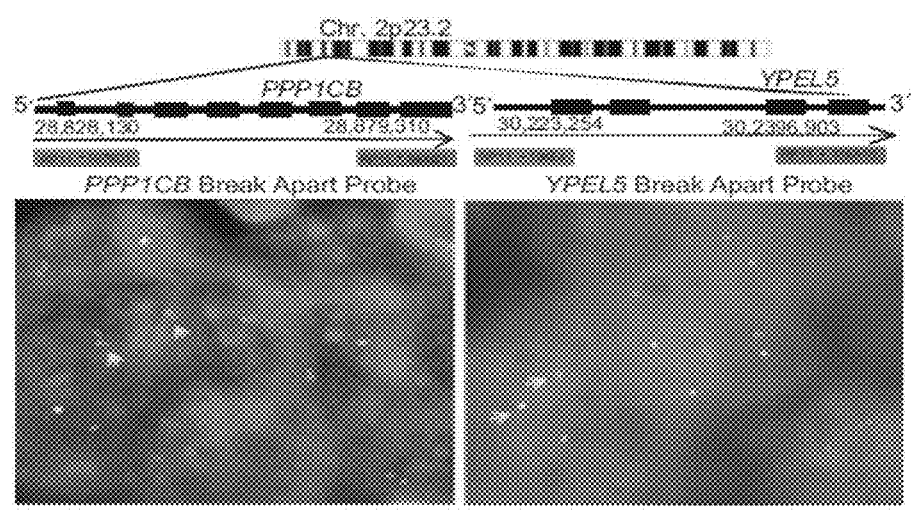
Figure 8:
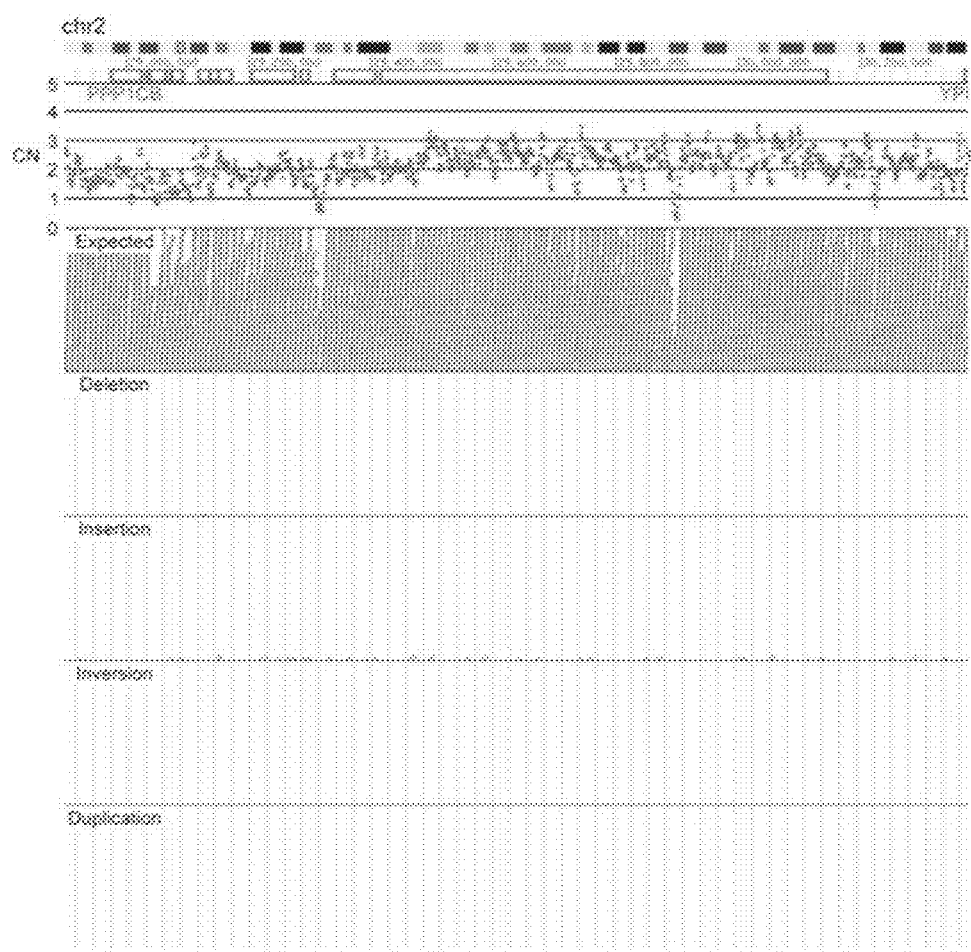
FIG. 8 shows whole-genome mate-pair sequencing results. (A) PPP1CB-YPEL5 region of chr2p for E84 (SI_3562). (B) Region of biallelic deletion of chr13q in E84 (SI_3562).
Figure 8:
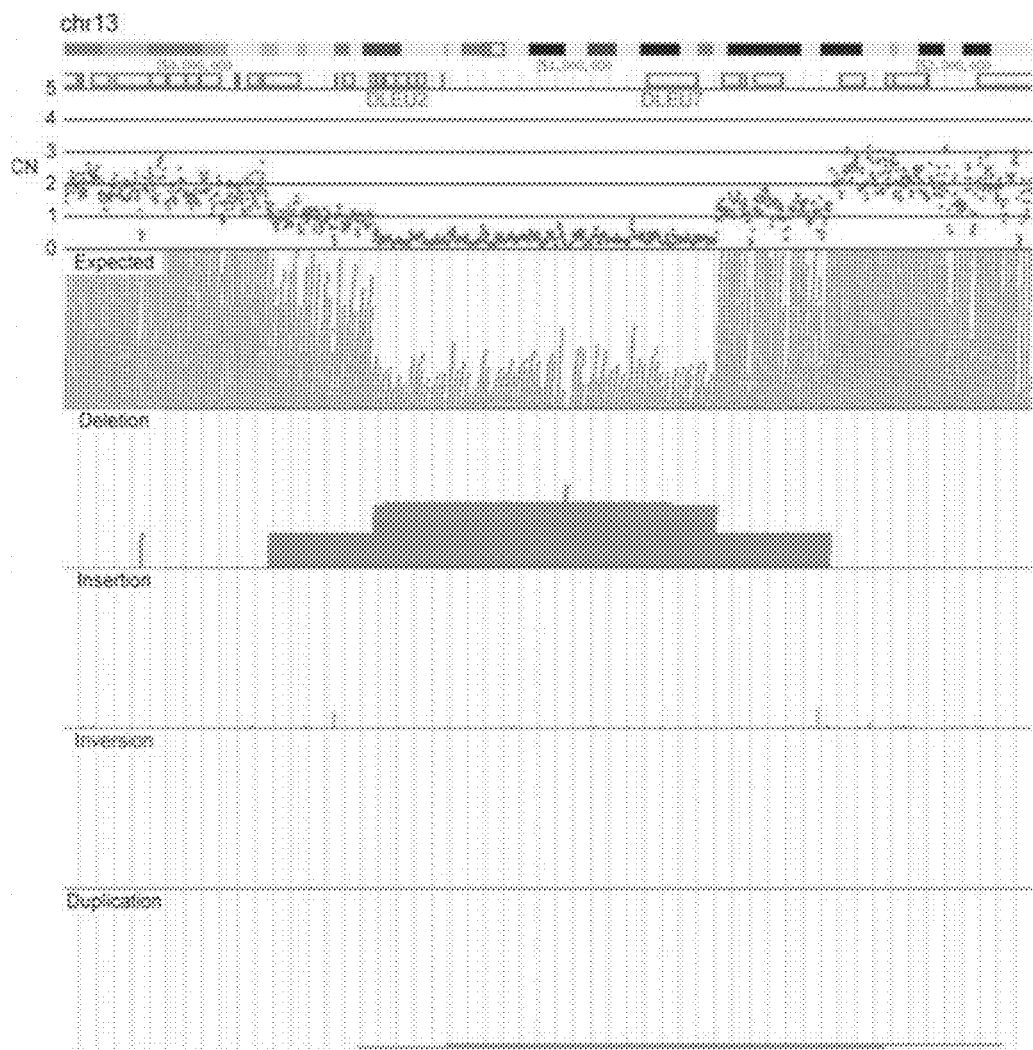

Genomic Analysis of YPEL5/PPP1CB Fusion. Whole genome mate-pair sequencing was performed on DNA isolated from two of the RNA chimera-positive index cases of CLL, to determine whether a genomic rearrangement was responsible for the YPEL5/PPP1CB and reciprocal chimeric transcripts. Although these studies revealed common structural alterations, such as deletion of 13q (FIG. 8B), extensive analysis revealed no evidence of a genomic basis for a juxtaposition of YPEL5 and PPP1CB or junctional sequences indicating a gene fusion between the two genes at the DNA level. The YPEL5, PPP1CB, and intervening loci showed a normal pattern of expected ~5-kb mate-pair spacings, representative of the source libraries, with no regions of apparent copy number gain or loss (FIG. 3 and FIG. 8B).

Figure 9:
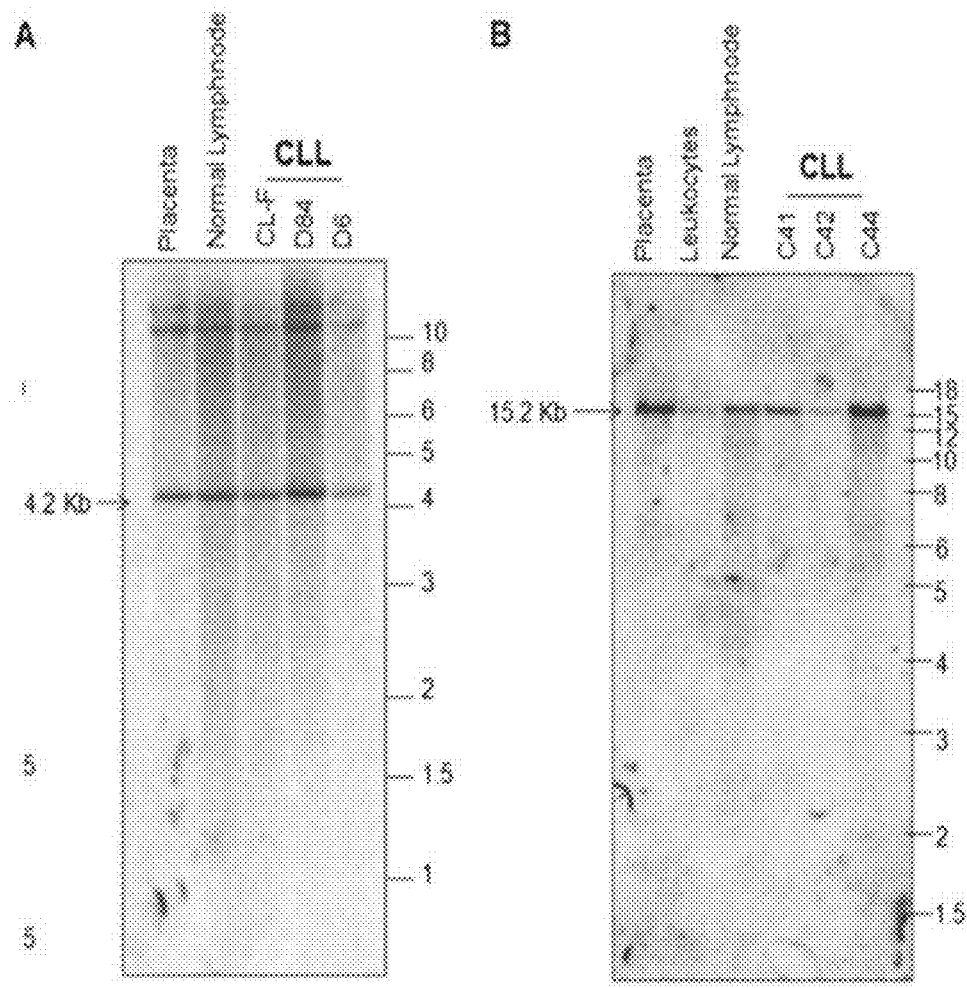
FIG. 9 shows (A) Southern blotting results for identifying genomic breakpoint in exon 2 of YPEL5 using Xba1 (4.2 kb). (B) Enzyme Nco1 was used to generate a large fragment (15.2 kb) that encompasses the entire YPEL5 gene to identify break points in case the fusion chimera is generated by YPEL5 transcript variant 4.
Figure 10:
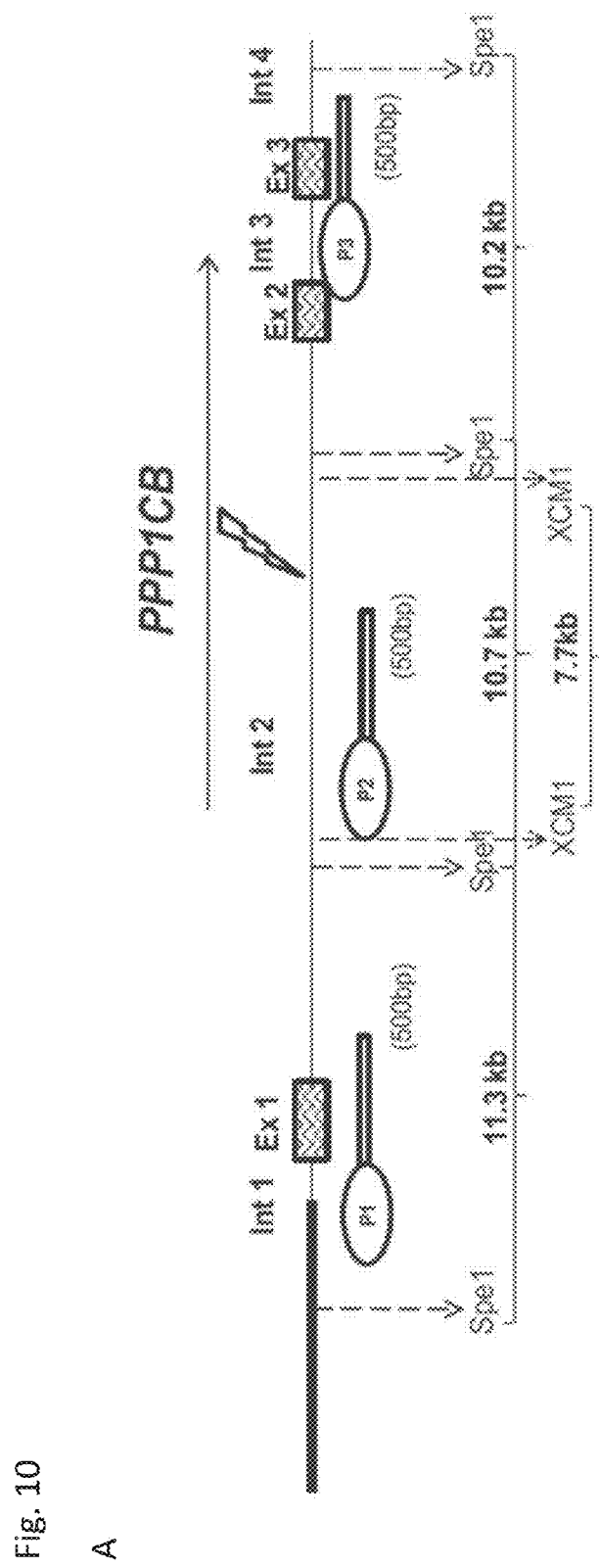
FIG. 10 shows (A) Restriction sites map depicting the sites targeted by different enzymes (Spe1 and XcM1) in intron 2 of PPP1CB. Because of the large size of intron 2 of PPP1CB, the restriction enzyme Spe1 was selected for generation of three independent ~10-kb fragments that are targeted separately (B, C, and D) by three different probes (P1, P2, and P3). (E) Fragment 2 targeted by P2 was independently analyzed by XcM1 to rule out the false-positive bands generated by Spe1.
Figure 10:
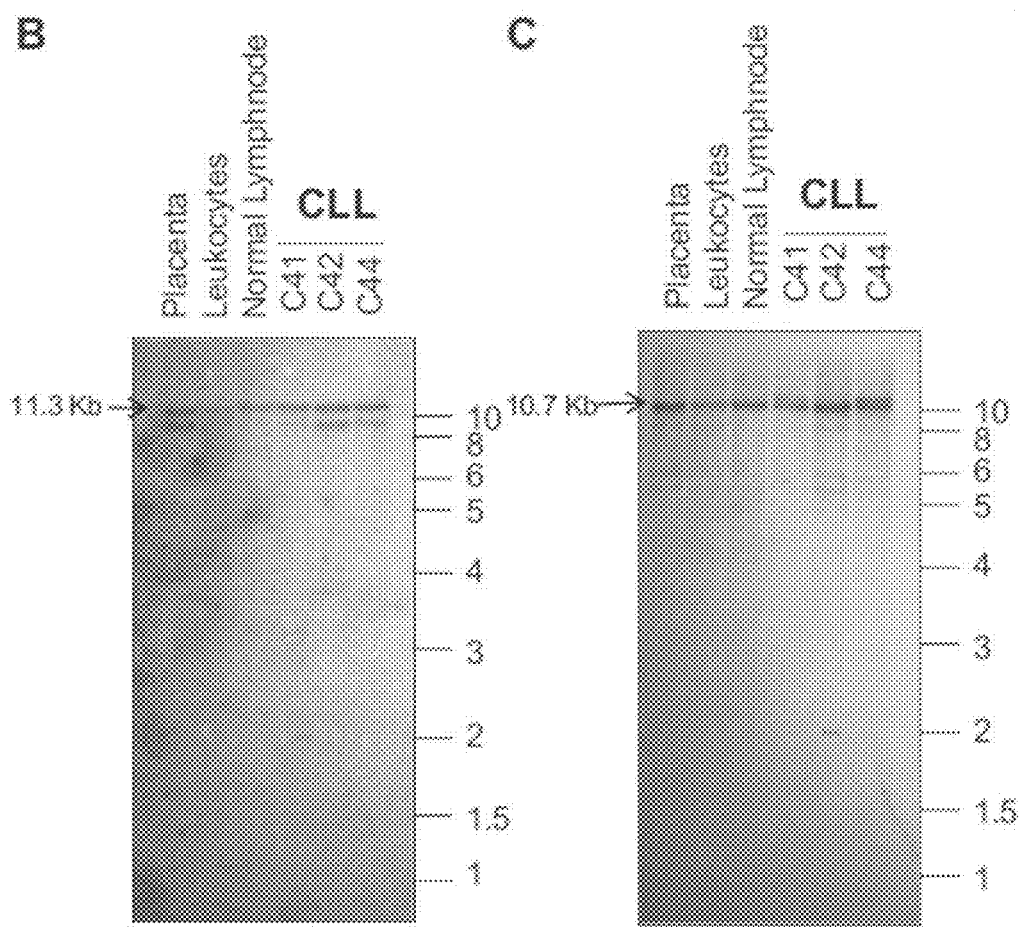
Figure 10:
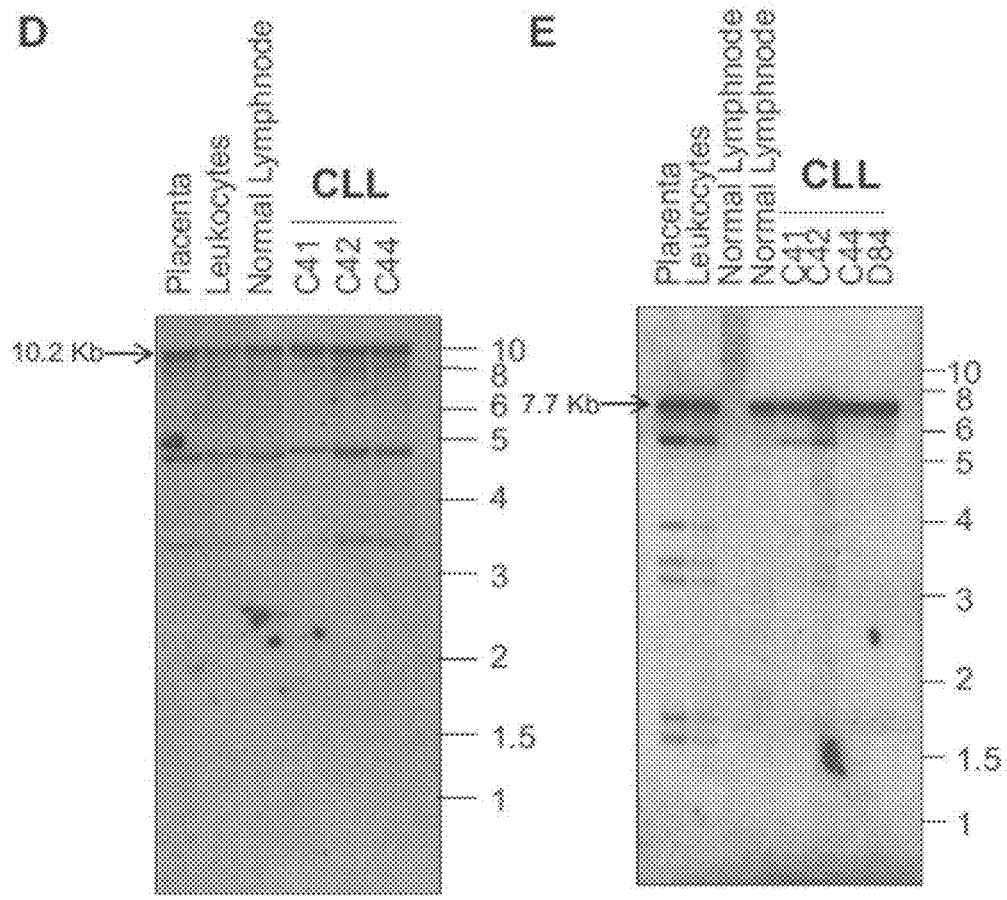

Southern blot hybridization was performed using DNA isolated from two of the index cases that yielded the YPEL5/PPP1CB fusion by paired-end transcriptome sequencing, to further investigate the origin of the YPEL5/PPP1CB fusion. Southern blot hybridization using a 0.5-kb-long probe targeting intron 2 of YPEL5 and DNA derived from the index samples did not reveal any novel nongerm line bands in independent experiments with three different restriction enzymes (EcoR1, Xba1, and Nco1) (FIG. 3B and FIGS. 9 A and B). Similarly, Southern blot hybridization of DNA of index samples with three different probes (0.5 kb) targeting intron 2 of PPP1CB using two different restriction enzymes (Spe1 and Xcm1) also did not show any such recombinations, indicative of absence of genomic rearrangements involving the PPP1CB locus (FIG. 10). These results are supportive of RNA splicing events as the basis for the YPEL5/PPP1CB chimera detected in CLLs by PETS and RT-PCR.

FISH was performed on interphase cells from YPEL5/PPP1CB-positive CLL samples using break-apart probes flanking the ends of YPEL5 and PPP1CB gene (FIG. 3D). The results show that both PPP1CB and YPEL5 probes stayed in close proximity to each other (FIG. 3D, yellow arrows), indicating absence of either copy number changes (amplification/deletion) or chromosomal rearrangements that result in breaking and dislocation of flanking probes.

IgH variable region sequencing was performed to determine the mutational status of the Ig genes expressed in 25 of the cases of CLL investigated in this study. These studies revealed that 52% of the cases were mutated, and 48% were unmutated. This indicates a comparable frequency of mutated and unmutated IgV cases in YPEL5/PPP1CB-positive cells.

Expression of Protein Products from the YPEL5/PPP1CB Fusion. The architecture of the YPEL5/PPP1CB fusion predicts the generation of a truncated PPP1CB protein product of 31 kDa (FIG. 5A). To investigate whether the YPEL5/PPP1CB chimeric transcript produces a functional protein product, the full-length fusion transcript from index samples was ampliefied and cloned into a mammalian expression vector. Introduction of these plasmids into HEK 293 cells resulted in synthesis of a truncated PPP1CB protein that was smaller in size compared with wildtype PPP1CB protein (FIG. 2D).

Figure 4:
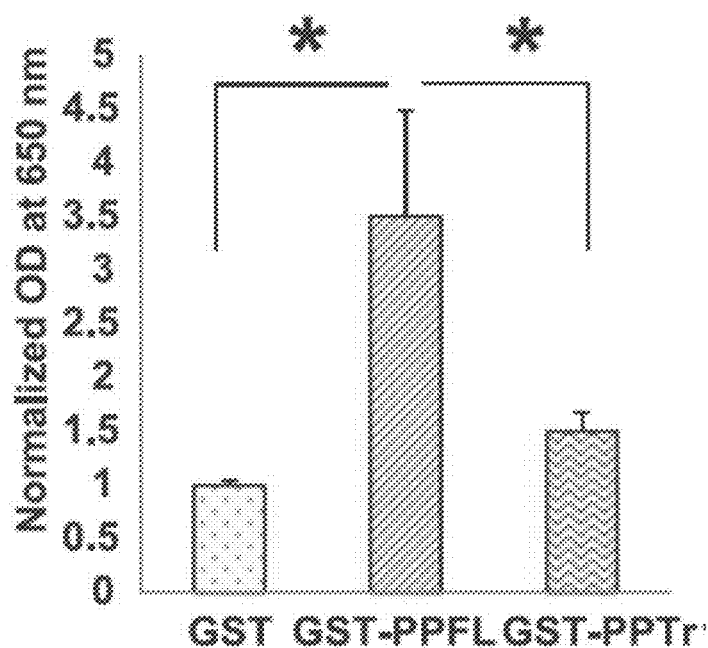
FIG. 4 shows activity of wild-type PPP1CB and truncated proteins. (A) Phosphatase activity of wild-type PPP1CB and truncated proteins. (B) Functional consequences of PPP1 CB down-regulation. (C) Colony-formation cell assays in MEC1 and JVM3 cells stably expressing control shRNA and PPP1CB depleting shRNA.
Figure 4:
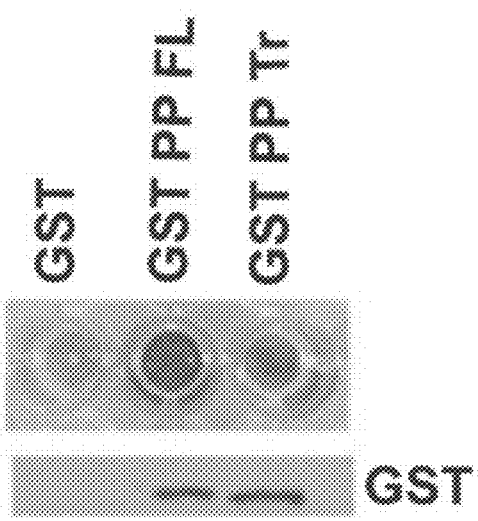
Figure 4:
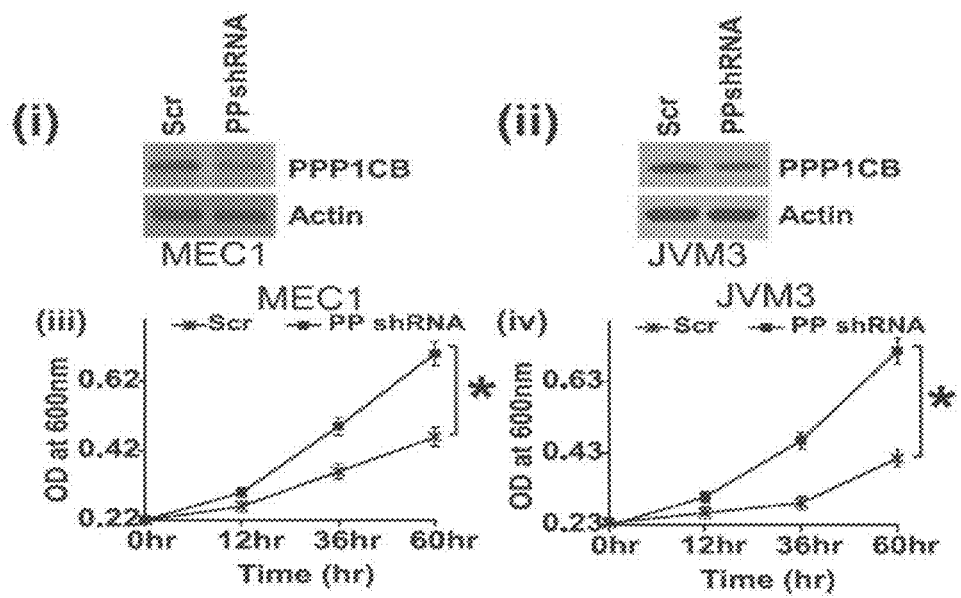
Figure 4:
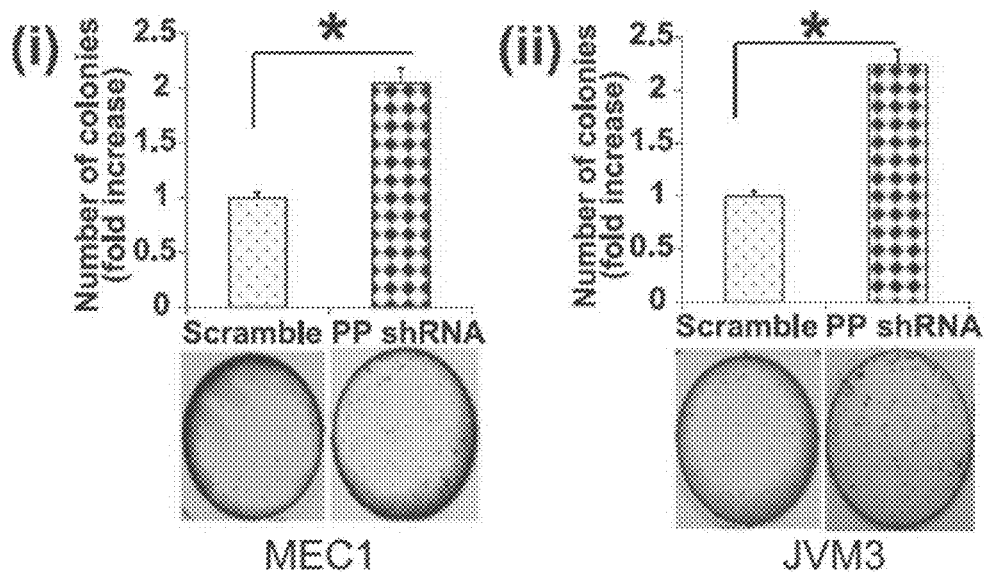

Functional Analysis of the YPEL5/PPP1CB Fusion Product. Recombinant full-length PPP1CB (wild-type, PP-FL) or mutant PPP1CB protein lacking N-terminal 28-aa (truncated, PP-Tr) proteins were expressed in Escherichia coli and their catalytic activity was assessed by performing an in vitro phosphatase assay, to determine whether truncation by the fusion causes functional activation or loss of PPP1CB. The results indicate that the truncated PPP1CB (PP-Tr) protein demonstrated significantly less phosphatase activity ($P<0.01$), as depicted by reduction in the absorbance compared with PP-FL (FIG. 4A). GST fusion proteins alone had very minimal cross-effects on the activity of the proteins. These results confirm that N-terminal truncation caused by YPEL5/PPP1CB fusion decreases the phosphatase activity of PPP1CB enzyme.

Figure 11:
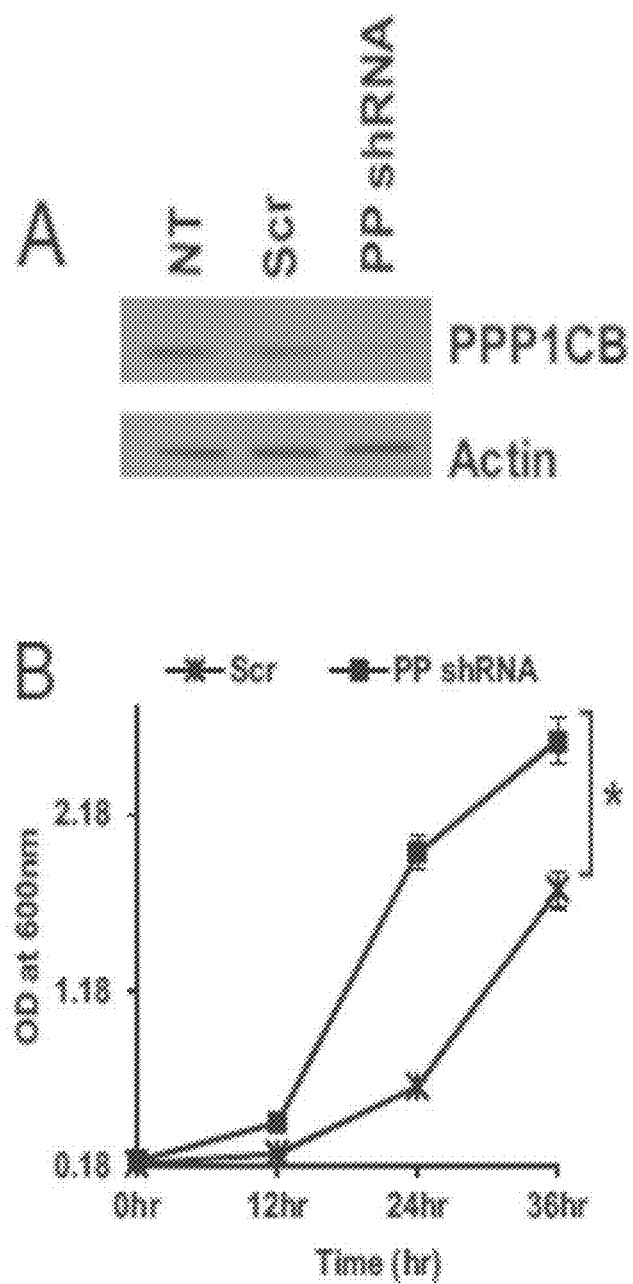
FIG. 11 shows functional consequences of PPP1 CB down-regulation. (A) A representative Western blot showing the knockdown efficiency of PPP1CB protein expression in stable NIH 3T3 cell lines expressing none or either of scramble and PPP1CB shRNA. WST cell proliferation assays in NIH 3T3 (B) and Ba/F3 (C) cells. (D) Colony-formation cell assays in Ba/F3 cells stably expressing control or shRNA and PPP1CB depleting shRNA.
Figure 11:
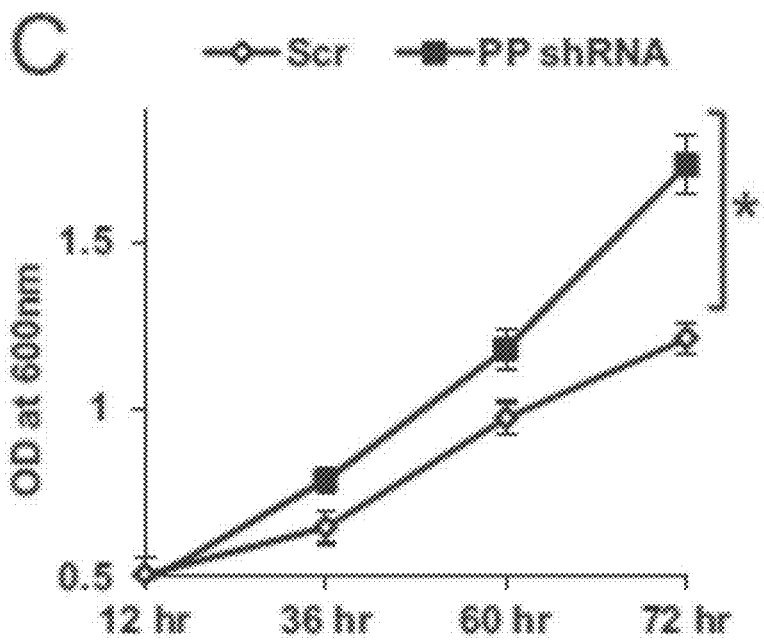
Figure 11:
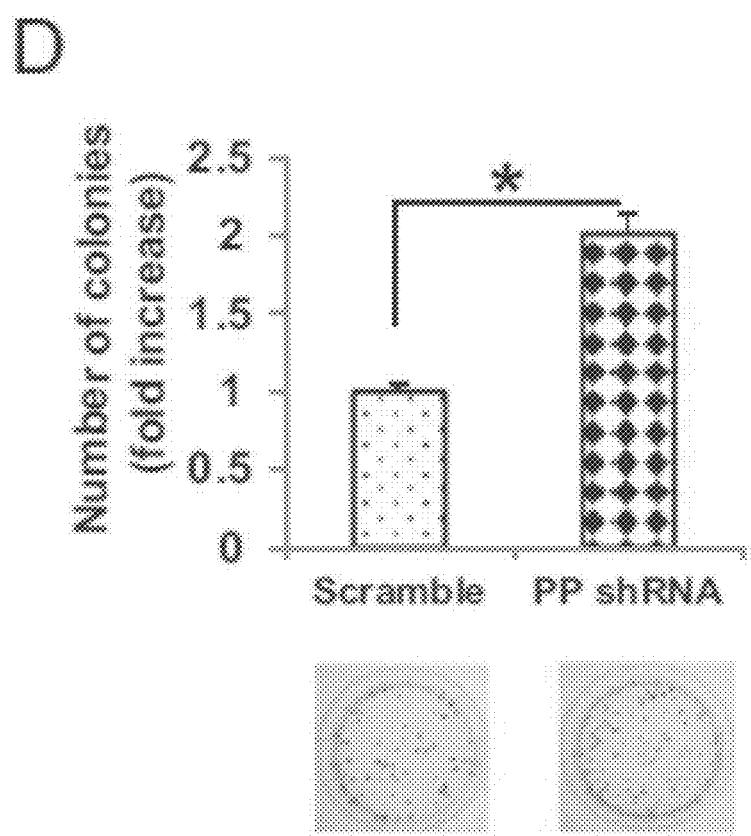

Given the demonstration of significantly diminished functional activity of the truncated PPP1CB encoded by the YPEL5/PPP1CB fusion, the biologic consequences of functional inactivation of PPP1CB were investigated by knocking down the expression of PPP1CB using a lentivirus-based shRNA approach and evaluating its effects on cell proliferation in B-lymphocytic leukemia cell lines MEC1 (Maher C A, et al. (2009) Transcriptome sequencing to detect gene fusions in cancer. Nature 458(7234):97-101) and JVM3 (24), as well as in National Institutes of Health (NIH) 3T3 and Ba/F3 cell lines. Water-soluble tetrazolium-1 (WST-1) cell proliferation assays demonstrated that in comparison with control ($P<0.01$), knockdown of PPP1CB resulted in increased cell proliferation in NIH 3T3 and Ba/F3 cells (FIG. 11). PPP1CB silencing also resulted in significant increases ($P<0.01$) in proliferation of both B-lymphocytic leukemia cell lines MEC1 and JVM3 (FIG. 4B).

Soft agar colony assays were performed using PPP1CB knockdown in the above-mentioned cell lines along with scramble shRNA-expressing cells as control. As shown in FIG. 4C and FIG. 11, PPP1CB silencing resulted in increased colony formation compared with control scramble shRNA-expressing cells ($P<0.01$). Overall, these functional studies show that impaired PPP1CB function promotes an oncogenic phenotype in mature B-cell lymphocytic leukemia-derived cells.

TABLE 3

| Chimera | Type | Status |
| --- | --- | --- |
| YPEL5/PPP1CB | Intrachromosomal | Recurrent |
| PPP1CB/YPEL5 | Intrachromosomal | Recurrent |
| CLPTM1L/SERBP1 | Intrachromosomal | Singleton |
| MTSS1/TATDN1 | Readthrough | Recurrent |
| SEPT6/NKRF | Readthrough | Recurrent |
| RAPGEF3/P11 | Readthrough | Recurrent |
| BC061919/MLL5 | Readthrough | Recurrent |
| MAP2K7/SNAPC2 | Readthrough | Recurrent |
| GAS7/RCVRN | Readthrough | Recurrent |

TABLE 4

| Sample ID | Age (y) | Sex | % WBC | % Lymphocytes | % CLL | Ig-VH | ZAP-70 | FISH |
| --- | --- | --- | --- | --- | --- | --- | --- | --- |
| Index cases | | | | | | | | |
| C-41 | 68 | F | 70.6 | 74 | 93 | 4-4, Mutated | Neg | Del 13q |
| D-50 | 56 | F | 91.1 | 93 | 97 | 3-30, Unmutated | Pos | |
| D-51 | 65 | F | 118 | 70 | 97 | 3-9, Mutated | Neg | Del 13q |
| E-58 | 78 | F | 110 | 85 | 97 | 4-b, Unmutated | Pos | |
| F-78 | 60 | M | 64.3 | 92 | 96 | 3-23, Unmutated | Pos | |
| Expansion set | | | | | | | | |
| C-38 | 64 | M | | 80 | 70 | 3-11, Unmutated | Pos | Del 13q |
| C-42 | 71 | F | | 79 | 88 | 1-46, Mutated | Neg | Trisomy 12 |
| C-44 | 57 | F | 96.4 | 82 | 94 | 1-3, Mutated | Neg | |
| C-61 | 71 | M | 50.8 | 84.7 | 90 | 1-69, Unmutated | Pos | Del 13q |
| C-75 | 63 | M | | 94 | 88 | 6-1, Mutated | Neg | |
| D-6 | 71 | M | | 89 | 90 | 3-72, Mutated | Neg | |
| D-14 | 84 | F | 25.8 | 93 | 98 | 1-69, Unmutated | Pos | |
| D-22 | 88 | F | | 84 | 91 | 2-26, Unmutated | Pos | |
| D-49 | 70 | F | 37.7 | 65.9 | 88 | 4-34, Mutated | Neg | Del 13q |
| D-80 | 43 | M | 34.9 | 63.7 | 89 | 4-59, Mutated | Neg | |
| D-84 | 58 | F | 15.5 | 71.5 | 78 | 4-34, UnMutated | Pos | Trisomy 12 |
| E-49 | 47 | F | 20.8 | 73 | 87 | Mutated | | |
| E-83 | 74 | F | 11.6 | 54 | 81 | 3-30, Unmutated | Neg/?+ | |
| E-84 | 86 | M | 40.8 | 81 | 93 | 6-1, Mutated | Indeterm | |
| F-12 | 89 | M | 16.5 | 36.8 | 58 | 4-39, Unmutated | Pos | Trisomy 12 |
| F-20 | 94 | F | | 81 | 92 | 3-33, Mutated | Neg | |
| F-24 | 65 | F | | 45 | 67 | 3-74, Mutated | Neg | Del 13q |
| F-50 | 62 | M | 71.4 | 82 | 94 | 1-69, Unmutated | Pos | |
| F-67 | 64 | F | | 63 | 83 | 3-48, Unmutated | Pos | |
| F-80 | 63 | M | 68.8 | 70.9 | 97 | 2-5, Mutated | Indeterm | |

F, female; Indeterm, indeterminate; M, male; Neg, negative; Pos, positive.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A kit for detecting RNA fusions associated with B-cell chronic lymphocytic leukemia in a subject, comprising or consisting essentially of: at least a first RNA fusion informative reagent for identification of an YPEL5-PPP1CB and an PPP1CB-YPEL5 RNA fusion.

2. The kit of claim 1, wherein said reagent is a probe that specifically hybridize to the fusion junction of an YPEL5-PPP1CB and an PPP1CB-YPEL5 RNA fusion, a pair of primers that amplify a fusion junction of an YPEL5-PPP1CB and an PPP1CB-YPEL5 RNA fusion, an antibody that binds to a truncated PPP1CB polypeptide, one or more sequencing primers that binds to a YPEL5-PPP1CB and an PPP1CB-YPEL5 RNA fusion and generate extension products that span the fusion junction of said YPEL5-PPP1CB and PPP1CB-YPEL5 RNA fusions, mass spectrometry reagents for identifying a truncated PPP1CB polypeptide, reagents for performing a PPP1CB activity assay, or a pair of probes wherein said first probe hybridizes to a YPEL5 nucleic acid and said second probe hybridizes to a PPP1CB nucleic acid.

3. The kit of claim 2, wherein said pair of primers comprises a first primer that hybridizes to a YPEL5 nucleic acid and second primer that hybridizes to a PPP1CB nucleic acid.

4. The kit of claim 1, further comprising one or more control nucleic acids.

5. The kit of claim 4, wherein said controls comprise mRNA fusions or cDNA equivalents thereof.

6. The kit of claim 1, wherein said reagent is labeled.

7. The kit of claim 1, wherein said YPEL5-PPP1CB RNA fusion comprises exon 1 of YPEL5 and exon 2 of PPP1CB.

8. The kit of claim 1, wherein said YPEL5-PPP1CB RNA fusion encodes a truncated PPP1CB polypeptide.

9. The kit of claim 8, wherein said truncated PPP1CB polypeptide consists of residue 29 to residue 327 of wild type PPP1CB.

10. The kit of claim 1, wherein said PPP1CB-YPEL5 RNA fusion comprises exon 1 of PPP and exon 3 of YPEL5.

11. The kit of claim 1, wherein said PPP1CB-YPEL5 RNA fusion encodes full-length wild-type YPEL5 protein.

* * * * *

UNITED STATES PATENT AND TRADEMARK OFFICE
CERTIFICATE OF CORRECTION

| | |
|---|---|
| PATENT NO. | : 9,657,350 B2 |
| APPLICATION NO. | : 14/271175 |
| DATED | : May 23, 2017 |
| INVENTOR(S) | : Kojo S J Elenitoba-Johnson et al. |

It is certified that error appears in the above-identified patent and that said Letters Patent is hereby corrected as shown below:

In the Claims

Column 63, Lines 6 and 7, Claim 10 reads: "The kit of claim 1, wherein said PPP1CB-YPEL5 RNA fusion comprises exon 1 of PPP and exon 3 of YPEL5."

HOWEVER, IT SHOULD READ:

Claim 10: "The kit of claim 1, wherein said PPP1CB-YPEL5 RNA fusion comprises exon 1 of PPP1CB and exon 3 of YPEL5."

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*